(12) United States Patent
Bonutti et al.

(10) Patent No.: US 10,159,590 B2
(45) Date of Patent: *Dec. 25, 2018

(54) TOE ORTHOSIS

(71) Applicant: BONUTTI RESEARCH, INC., Effingham, IL (US)

(72) Inventors: Boris P. Bonutti, Effingham, IL (US); Peter M. Bonutti, Manalapan, FL (US); Kevin R. Ruholl, Teutopolis, IL (US); Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 390 days.

This patent is subject to a terminal disclaimer.

(21) Appl. No.: 14/991,387

(22) Filed: Jan. 8, 2016

(65) Prior Publication Data

US 2016/0120684 A1    May 5, 2016

Related U.S. Application Data

(63) Continuation of application No. 14/324,365, filed on Jul. 7, 2014, now Pat. No. 9,237,962, which is a
(Continued)

(51) Int. Cl.
*A61F 5/01* (2006.01)
*A61F 5/00* (2006.01)

(52) U.S. Cl.
CPC .............. *A61F 5/0127* (2013.01); *A61F 5/00* (2013.01); *A61F 5/019* (2013.01);
(Continued)

(58) Field of Classification Search
CPC .. A61F 2005/0153; A61F 5/00; A61F 5/0127; A61F 2002/5004; A61F 2002/503; A61F 2002/5033; A61F 2002/5075; A61F 2002/6818; A61F 2002/7625; A61F 2002/701; A61F 2/6607; A61F 2002/704; A61F 2002/7635; A61F 2/68; A61F 2002/5018; A61F 2002/7645; A61F 2/72;
(Continued)

(56) References Cited

U.S. PATENT DOCUMENTS 2,250,493 A * 7/1941 Milne ................. A61F 5/14
482/79
2,531,486 A   11/1950 Weber
(Continued)

*Primary Examiner* — Tarla Patel
(74) *Attorney, Agent, or Firm* — Stinson Leonard Street LLP

(57) ABSTRACT

An orthosis configured to stretch tissue around an ankle joint of a patient and methods for assembling and using the same are provided. The orthosis includes a first member affixable to a lower leg of the patient, a second member affixable to a foot of the patient, the second member including a second extension member having an arcuate shape configured to move along an arcuate path relative to the first member when the second member is moved from a first position to a second position relative to the first member, and a drive assembly coupled to the first member and the second member, the drive assembly configured to move the second member with respect to the first member.

14 Claims, 24 Drawing Sheets

Related U.S. Application Data continuation of application No. 13/585,917, filed on Aug. 15, 2012, now Pat. No. 8,771,211, which is a continuation of application No. 11/686,989, filed on Mar. 16, 2007, now Pat. No. 8,251,935.

(60) Provisional application No. 60/783,248, filed on Mar. 17, 2006.

(52) U.S. Cl.
CPC ............ *A61F 2005/0139* (2013.01); *A61F 2005/0153* (2013.01); *A61F 2005/0155* (2013.01); *Y10T 29/49826* (2015.01)

(58) Field of Classification Search
CPC .......... A61F 2002/764; A61F 2002/705; A61F 5/0111; A61F 2/66; A61F 5/019; A61F 2005/0155; A61F 2005/0139; A61F 5/0113; A61F 5/0116; A61F 5/0118; A61F 2005/0148; A61F 2005/0146; A61F 2005/0151; A61F 5/0195; A45F 3/06; A45F 3/08; F03G 5/06; H02N 2/18; Y10S 310/80; A61H 1/0266; A61H 2001/027; Y10T 29/49826
USPC ........................... 602/30, 27; 601/27; 482/79
See application file for complete search history.

(56) References Cited

U.S. PATENT DOCUMENTS

| | | | |
|---|---|---|---|
| 4,263,902 A | | 4/1981 | Dieterich |
| 4,862,875 A | * | 9/1989 | Heaton ................ A61H 1/0266 482/79 |
| 5,052,379 A | | 10/1991 | Airy et al. |
| 5,094,226 A | * | 3/1992 | Medcalf ............... A61H 1/0266 601/104 |
| 5,117,814 A | | 6/1992 | Luttrell et al. |
| 5,297,540 A | * | 3/1994 | Kaiser .................. A61H 1/0266 482/79 |
| 5,399,147 A | | 3/1995 | Kaiser |
| 5,437,619 A | | 8/1995 | Malewicz et al. |
| 5,472,410 A | | 12/1995 | Hamersly |
| 5,520,620 A | | 5/1996 | Johnson |
| 5,575,764 A | | 11/1996 | Van Dyne |
| 5,749,840 A | | 5/1998 | Mitchell et al. |
| 6,001,075 A | | 12/1999 | Clemens et al. |
| 6,171,272 B1 | | 1/2001 | Akita et al. |
| 6,350,246 B1 | | 2/2002 | DeToro et al. |
| 6,824,523 B2 | | 11/2004 | Carlson |
| 7,473,234 B1 | | 1/2009 | Weltner et al. |
| 7,517,330 B2 | | 4/2009 | Deharde et al. |
| 8,251,935 B2 | * | 8/2012 | Bonutti ................ A61F 5/0127 602/23 |
| 8,771,211 B2 | * | 7/2014 | Bonutti ................ A61F 5/0127 602/16 |
| 9,237,962 B2 | * | 1/2016 | Bonutti ................ A61F 5/0127 |
| 2007/0219475 A1 | | 9/2007 | Bonutti et al. |

* cited by examiner

TOE ORTHOSIS

CROSS-REFERENCE TO RELATED APPLICATION

This patent application is a continuation application of U.S. patent application Ser. No. 14/324,365, filed on Jul. 7, 2014 (now U.S. Pat. No. 9,237,962), which is a continuation application of U.S. patent application Ser. No. 13/585,917, filed on Aug. 15, 2012 (now U.S. Pat. No. 8,771,211), which is a continuation application of U.S. patent application Ser. No. 11/686,989 filed on Mar. 16, 2007 (now U.S. Pat. No. 8,251,935), which claims priority from U.S. Provisional Patent Application Ser. No. 60/783,248, filed on Mar. 17, 2006, the contents of which are herein incorporated by reference in its entirety.

FIELD OF THE DISCLOSURE

The present disclosure relates to an adjustable orthosis for stretching tissue in the human body. In particular, the present disclosure relates to an adjustable orthosis which can be used for stretching tissue such as ligaments, tendons or muscles around a joint during flexion or extension of the joint.

BACKGROUND

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to correct this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include: U.S. Pat. No. 6,599,263, entitled "Shoulder Orthosis;" U.S. Pat. No. 6,113,562, entitled "Shoulder Orthosis;" U.S. Pat. No. 5,848,979, entitled "Orthosis;" U.S. Pat. No. 5,685,830, entitled "Adjustable Orthosis Having One-Piece Connector Section for Flexing;" U.S. Pat. No. 5,611,764, entitled "Method of Increasing Range of Motion;" U.S. Pat. No. 5,503,619, entitled "Orthosis for Bending Wrists;" U.S. Pat. No. 5,456,268, entitled "Adjustable Orthosis;" U.S. Pat. No. 5,453,075, entitled "Orthosis with Distraction through Range of Motion;" U.S. Pat. No. 5,395,303, entitled "Orthosis with Distraction through Range of Motion;" U.S. Pat. No. 5,365,947, entitled "Adjustable Orthosis;" U.S. Pat. No. 5,285,773, entitled "Orthosis with Distraction through Range of Motion;" U.S. Pat. No. 5,213,095, entitled "Orthosis with Joint Distraction;" and U.S. Pat. No. 5,167,612, entitled "Adjustable Orthosis;" U.S. patent application Ser. No. 11/261,424 entitled "Range of Motion Device;" and PCT International Application No. PCT/US06/60228 entitled "Range of Motion Device," all to Bonutti and herein are expressly incorporated by reference in their entirety

SUMMARY

The present disclosure provides an ankle orthosis for stretching the connective tissue around an ankle joint of a patient. An ankle joint defines on one side of the joint an inner sector which decreases in angle as the joint is flexed in a first direction (dorsiflexion) and on the opposite side of the joint an outer sector which decreases in angle as the joint is flexed in second direction (plantarflexion).

The orthosis includes a first member affixable to a lower leg of the patient. A second member is affixable to a foot of the patent, where the heel of the foot is free floating. The first member includes a first extension member which defines an arcuate channel therein. The second a member has a second extension member having an arcuate shape extending there from. The second and first extension members are operatively connected, such that the second extension member travels through arcuate channel of the first extension member when the second member is moved from a first position to a second position relative to the first member.

The orthosis further includes a drive assembly for selectively moving the second extension member relative to the first extension member. The drive assembly is mounted onto the first extension member, engaging the second extension member. The drive assembly can be manually or automatically actuated to selectively move the second extension member relative to the first extension member.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

The present disclosure relates to an orthosis for moving a joint between first and second relatively pivotable body portions. A joint and the first and second body portions can define on one side of the joint an inner sector which decreases in angle as the joint is flexed in a first direction (dorsiflexion) and on the opposite side of the joint an outer sector which decreases in angle as the joint is flexed in second direction (plantarflexion).

The orthosis of the present disclosure includes a drive assembly for moving the second body portion with respect to the first body portion from a first position to a second position. The orthosis fully or at least partially restricts motion of the second body portion in at least one direction utilizing the principles of stress relaxation to stretch the tissue around the joint.

After a set time period, the drive assembly may be used to move the second body portion from the second position to a third position, incrementally stretching the tissue surrounding the joint. Thus, the orthosis may be capable of moving from a first position to one or more other positions to provide different configuration angles of the device. It is contemplated that the drive assembly may be used to incrementally move the second body portion after the expiration of a predetermined time or until completion of the protocol. This approach is different from application of a constant load over a sustained time period.

Figure 1:
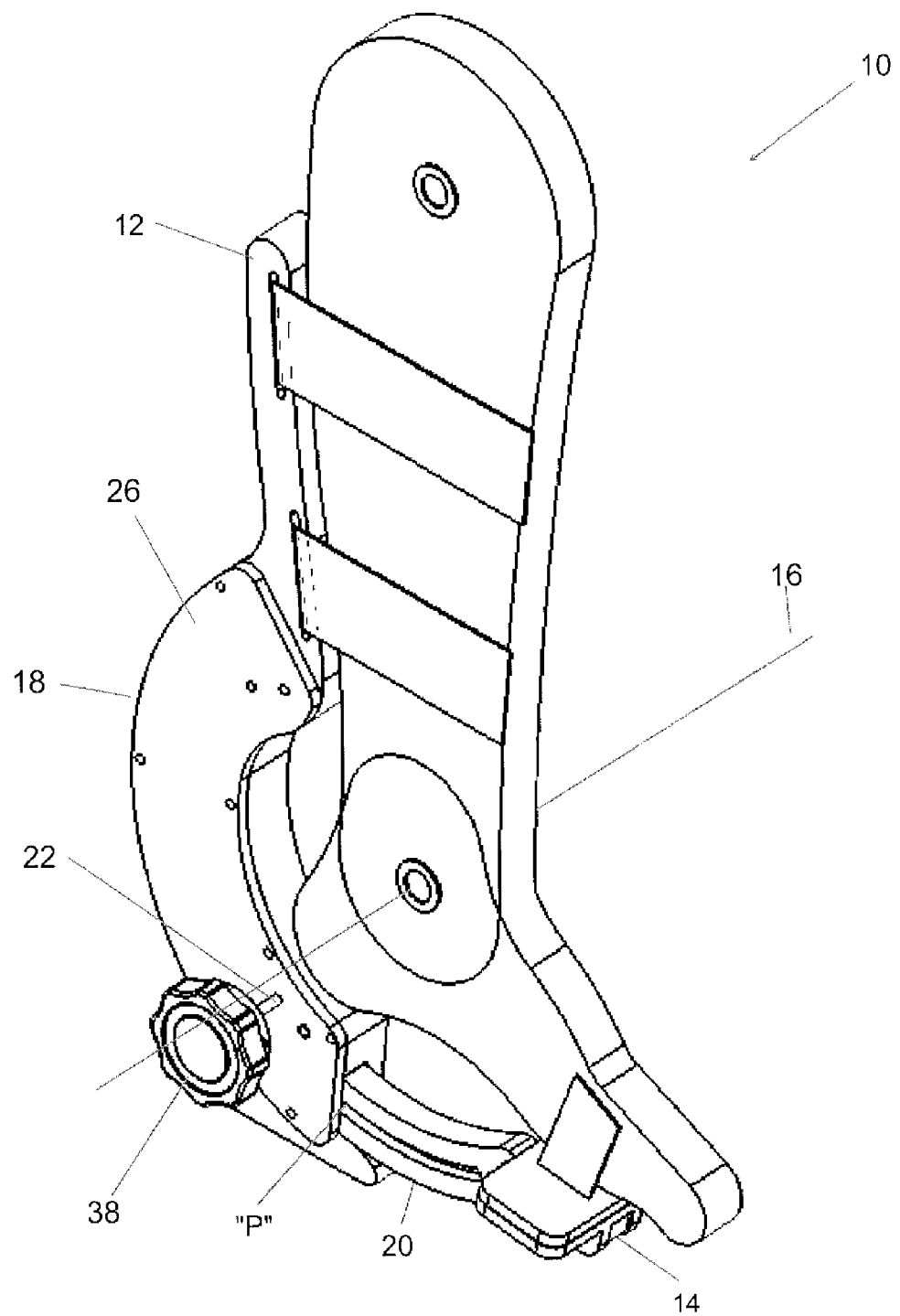
FIG. 1 depicts an isometric view of an orthosis of the present disclosure.

Referring now to the figures in which like reference designators refer to like elements, there is shown in FIG. 1 an orthosis 10 of the present invention. The orthosis 10 includes a first member 12 attachable to a first body portion, such as a user's lower leg. The shape and configuration of the first member 12 may be selected to support or conform generally along the lower leg of the user.

The first member 12 is operatively associated with or connected to a second member 14 so that the first and second members 12 and 14 may move or rotate with respect to each other. In use, the second member 14 may be attachable to a second body portion, such as a foot, so that the relative movement of the two members 12 and 14 also causes movement of the ankle joint. The orthosis 10 may have an axis of rotation 16 that is aligned with the axis of rotation of the joint. In this manner, the instantaneous axis of rotation (IAR) of the first and second members 12 and 14 may better match the IAR of the treated joint. The first and second members 12 and 14 are operatively connected to each other, offset from the orthosis axis 16.

The first member 12 of the orthosis 10 includes a first extension member 18 extending there from and having an arcuate shape. The second member 14 of the orthosis 10 likewise includes a second extension member 20 extending therefore and having an arcuate shape. The first and second extension members 18 and 20 are operatively connected at point "P," such that in operation the second extension member 20 travels through the first extension member 18 about an arcuate path and substantially through point "P." The arcuate shapes of the first and second extension members 18 and 20 result in the foot rotating about the orthosis axis 16, or alternatively about a moving IAR, when the second member 14 is moved from a first position to a second position relative to the first member 12, thereby preventing compression of the joint.

The orthosis 10 further includes a drive assembly 22, which is illustrated in FIG. 1 at or near point "P." In this embodiment, the drive assembly 22 is operably connected to the first and second extension members 18 and 20 for applying force to the first and second members 12 and 14 to pivot the second body portion about the orthosis axis 16. As will be shown below in additional embodiments, the drive assembly 22 may be configured or disposed to interact with or operate on one of the first or second members 12 and 14 independently.

Figure 2:
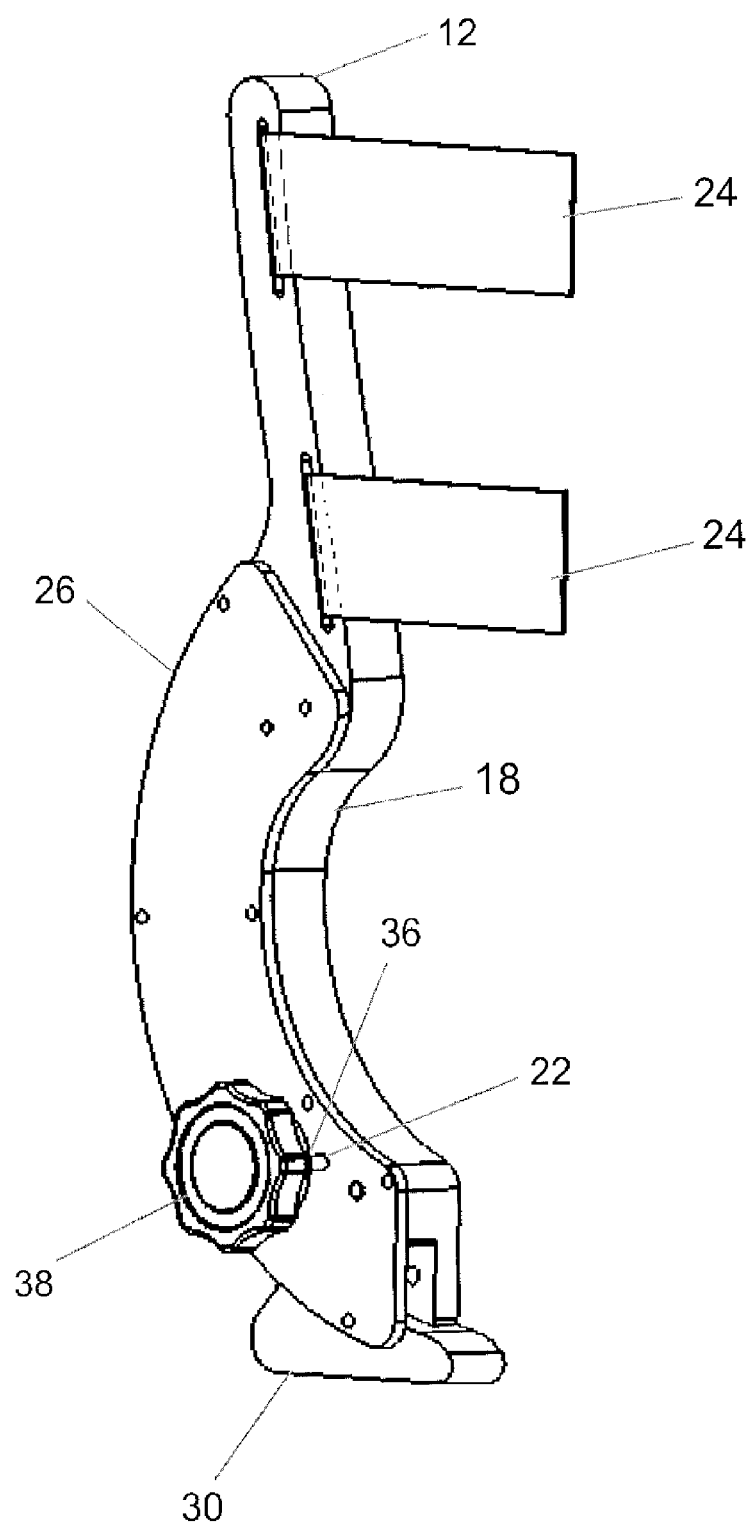
FIG. 2 depicts an isometric view of a first member of the orthosis of FIG. 1.

Referring to FIG. 2, in order for the orthosis 10 to flex the joint the first and second members 12 and 14 are affixed to the first and second body portions, respectively, tightly enough so that the first and second members 12 and 14 can apply torque to flex the joint. The attachments of the first and second body portions to the first and second members 12 and 14, allow the heel or the foot to be free-floating within the orthosis, thereby preventing heel lift-off during operation of the orthosis 10. The second extension member 20 is moved through the drive assembly 22 from a first position to a second position, relative to the first extension member 18, rotating the second member 14 and the second body portion about the orthosis axis 16 stretching the joint. As the second member 14 is rotated to the second position, the second extension member 20 travels at least partially through point "P" and may travel substantially through this point for a large range of motion. Because the first and second members 12 and 14 are affixed to the first and second body portions, the outward pivoting movement of the second member 14 causes the joint to be flexed as desired. The orthosis 10 may then be maintained in the second position for a predetermined treatment time providing a constant stretch to the joint. The orthosis 10 may alternatively be configured to impart a constant force or load on the joint or may utilize the techniques of Static Progressive Stretch as described in co-pending application Ser. No. 11/203,516, entitled "RANGE OF MOTION SYSTEM AND METHOD," and filed on Aug. 12, 2005, the entirety of which is incorporated by reference.

Returning to the example where the orthosis is maintained in the second position, after the expiration of the treatment time, the second member 14 may then be moved back to the first position, relieving the joint. Optionally, the second member 14 can be rotated to a third position, increasing the stretch on the joint, or partially reducing it to allow limited relaxation of the surrounding tissue. The second member 14 can be rotated at discrete time intervals to incrementally increase, reduce, or vary the stretch of the joint through the treatment cycle. After completion of the treatment cycle, the second member 14 is returned to the first position for removal of the orthosis 10. In operation, the orthosis 10 can be utilized to flex the joint in either dorsiflexion or plantarflexion.

Figure 3:
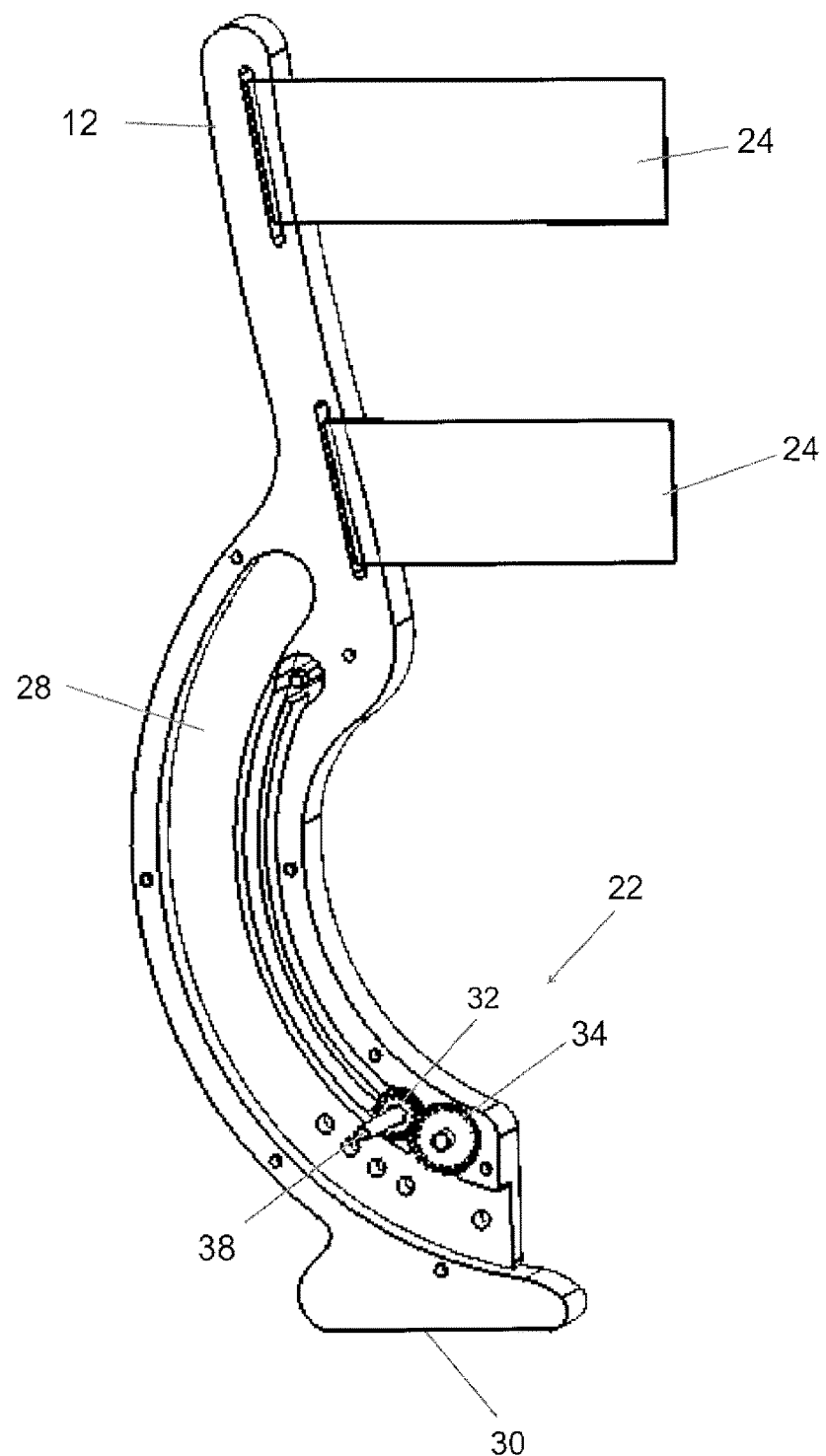
FIG. 3 depicts a sectional side view of the first member of FIG. 2.

Referring to FIGS. 2 and 3, the first member 12 includes a pair of straps 24 attachable about a user's lower leg. The straps 24 are sufficiently tighten to prevent relative movement between the first member 12 and the lower leg. The first extension member 18 portion of the first member 12 includes an arcuate main channel 28 extending therein. A cover plate 26 is affixable to the first extension member 18, over the main channel 28, defining a passage through which the second extension member 20 travels. The first extension member 18 can further include a base 30, where the base 30 is configured to support the orthosis 10 on a flat surface.

Figure 4:
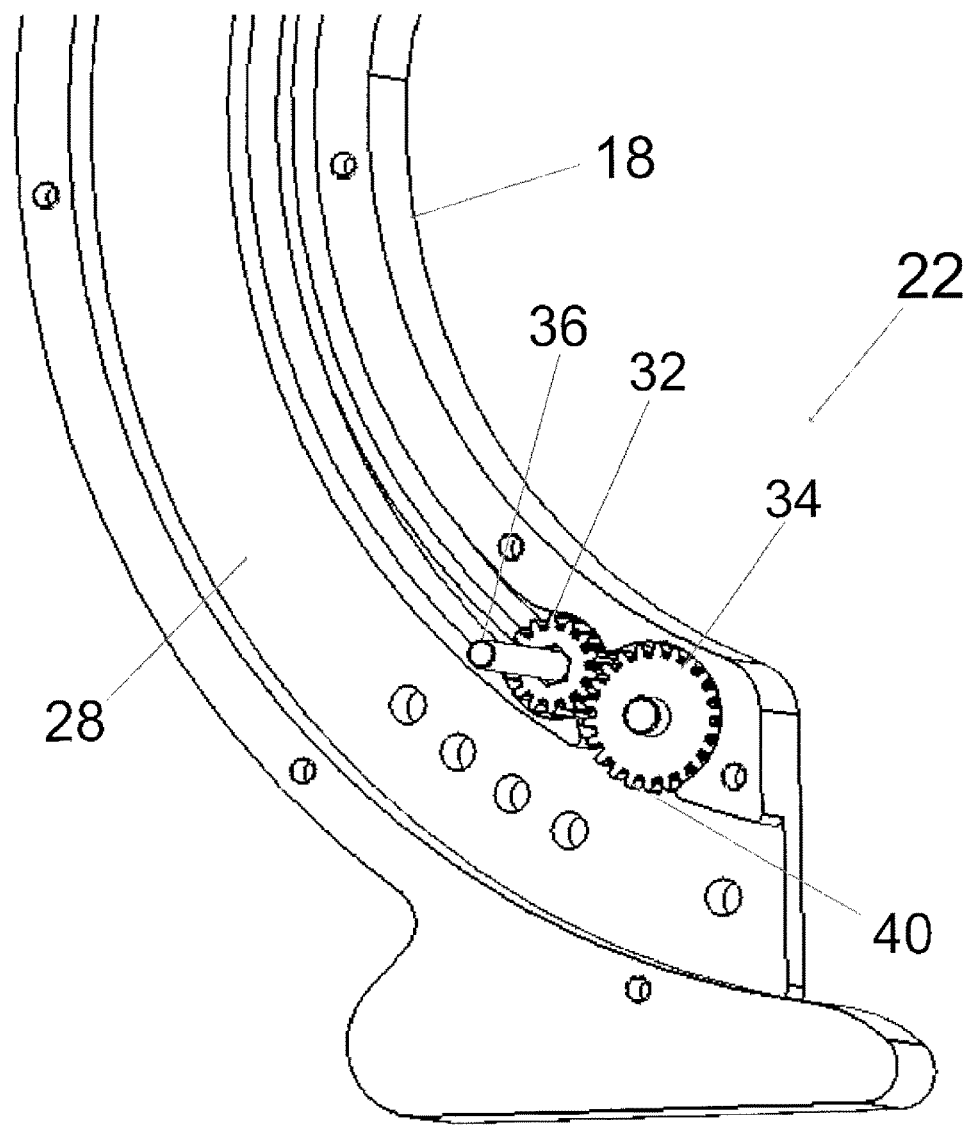
FIG. 4 depicts a partial sectional view of the first member of FIG. 2.

Referring also to FIG. 4, the drive assembly 22 is positioned in the first extension member 18 portion of the first member 12, proximal to the base 30. The drive assembly 22 includes a drive gear 32 and a main gear 34, where the teeth of the drive gear 32 engage the teeth of the main gear 34. A drive shaft 36 is connected to the drive gear 32, extending through the cover plate 26. A knob 38 can be affixed to the drive shaft 36 to facilitate rotation thereof. A rotation of the dive shaft 36 rotates the drive gear 32, which in turn rotates the main gear 34. The main gear 34 is sized such that a portion of the gear teeth 40 protrudes into the main channel 28 of the first extension member 18. The gear teeth 40 sufficiently protrude into the main channel 28, such that the gear teeth 40 can engage the second extension member 20.

The drive mechanism 22 can further include a locking mechanism. The locking mechanism can be used to secure the position of the second member 14 with respect to the first member 12. The locking mechanism can prevent the actuation of the drive mechanism 22, securing the position of first and second members 12 and 14. Alternatively, the locking mechanism can secure the first and second members 12 and 14, preventing an actuation of the drive mechanism 22 from moving the first and second members 12 and 14. The locking mechanism can be utilized such that the orthosis 10 can be used as a static splint.

Figure 5:
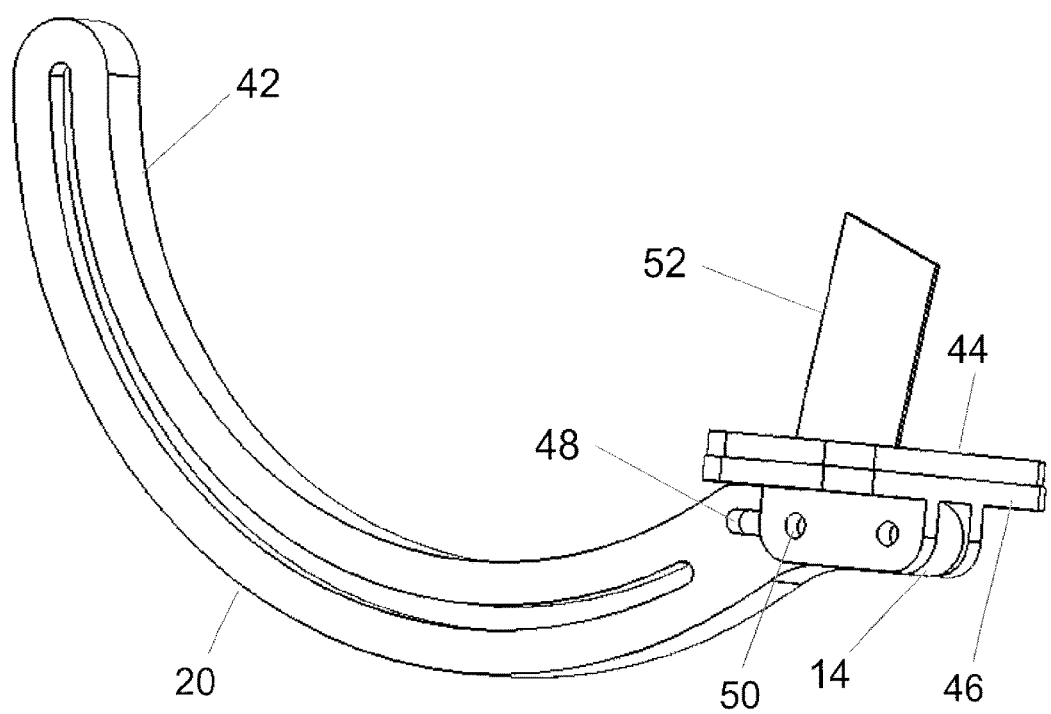
FIG. 5 depicts an isometric view of a second member of the orthosis of FIG. 1.
Figure 6:
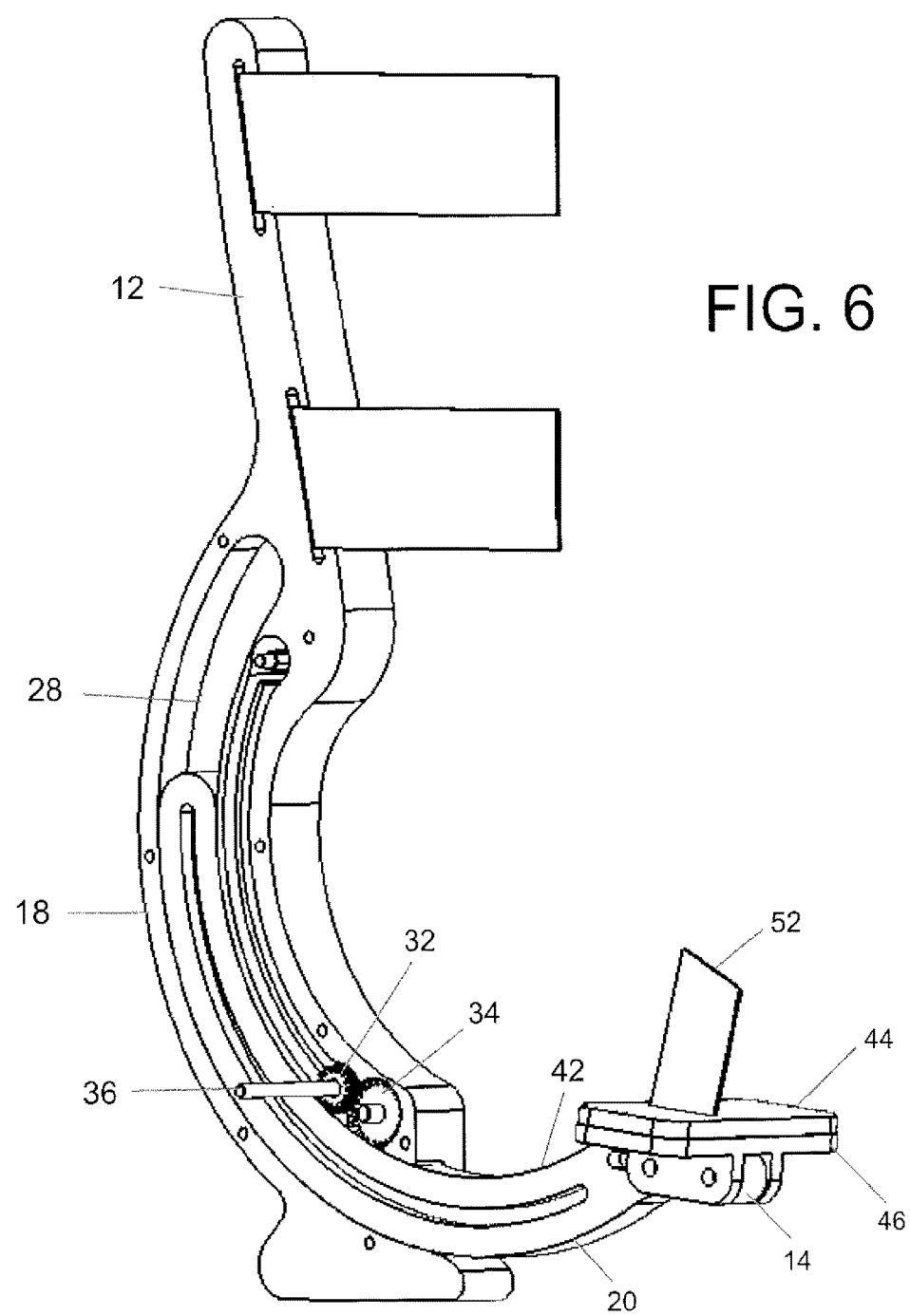
FIG. 6 depicts a sectional view of the orthosis of FIG. 1.

Referring to FIGS. 5 and 6, the second extension member 20 of the second member 14 includes an upper surface 42, where the upper surface 42 can include a plurality of teeth (not shown). The teeth are sized such that the gear teeth 40 of the main gear 34 can engage the upper surface 42 of the second extension member 20 to move the second extension member 20 through the arcuate passage in the first extension member 18 as the knob 38 is rotated.

The second member 14 can include a foot plate 44 slidingly mounted thereon. For example, the second member 14 can include a slotted section 48. A foot plate mounting bracket 46 is slidingly positioned on the second member 14, about the slotted section 48. Pins 50 are applied through the mounting bracket 46 to secure the mounting bracket 46 in the slotted section 48. The foot plate 44 can further include a strap 52 attachable about a user's foot. The strap 52 is sufficiently tightened to prevent relative movement between the foot plate 44 and the foot. The slidingly mounting of the foot plate 44 to the second member permits the foot plate to be adjustable to accommodate various size feet.

In an exemplary use, the orthosis 10 is operated to flex a joint in dorsiflexion in the following manner. The first member 12 is fastened to the lower leg and the second member 14 is fastened to the foot. The orthosis 10 is attached to the lower leg and foot in a first position. The drive assembly 22 is operated to move the second member 14 from the first position to a second position, relative to the first member 12 by rotating the foot about a joint axis 16, where the second extension member 20 in drawn in the arcuate passage of the first extension member 18. The connective tissue of the joint is consequently stretched. The orthosis 10 is maintained in the second position for a predetermined treatment time, utilizing the principles of stress relaxation to stretch the connective tissue of the joint. Additionally, the second extension member 20 can be made of a substantially rigid but flexible material, such that while in the second position the second extension member 20 acts like a spring, providing dynamic stretch to the connective tissue of the joint. After the expiration of the treatment time, the second member 14 may be returned to the first position, relieving the joint.

Optionally, the second member 14 can be rotated to a third position, further increasing the stretch of the connective tissue of the joint. The second member 14 can be rotated at discrete time intervals to incrementally increase the stretch of the joint through the treatment cycle. After completion of the treatment cycle, the second member 14 is returned to the first position relieving the joint.

In an exemplary use, the orthosis 10 is operated to flex a joint in plantarflexion in the following manner. The first member 12 is fastened to the lower leg and the second member 14 is fastened to the foot. The orthosis 10 is attached to the lower leg and foot in a first position. The drive assembly 22 is operated to move the second member 14 from the first position to a second position, relative to the first member 12 by rotating the foot about a joint axis 16, where the second extension member 20 is extended from the arcuate passage of the first extension member 18. The connective tissue of the joint is consequently stretched. The orthosis 10 is maintained in the second position for a predetermined treatment time, utilizing the principles of stress relaxation to stretch the connective tissue of the joint. Additionally, the second extension member 20 can be made of a substantially rigid but flexible material, such that while in the second position the second extension member 20 acts like a spring, providing dynamic stretch to the connective tissue of the joint. After the expiration of the treatment time, the second member 14 may be returned to the first position, relieving the joint.

Optionally, the second member 14 can be rotated to a third position, further increasing the stretch of the connective tissue of the joint. The second member 14 can be rotated at discrete time intervals to incrementally increase the stretch of the joint through the treatment cycle. After completion of the treatment cycle, the second member 14 is returned to the first position relieving the joint.

Figure 7:
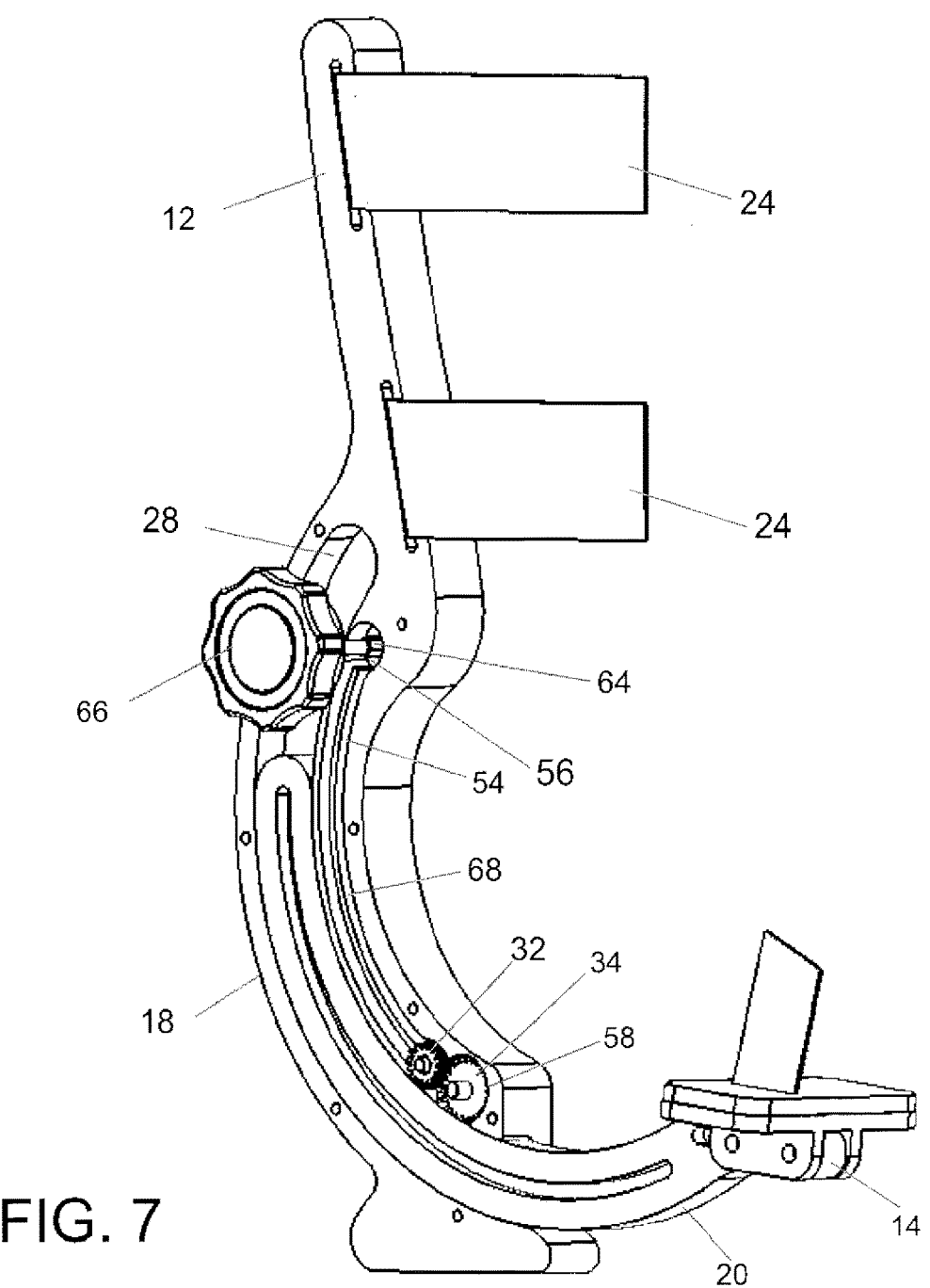
FIG. 7 depicts an alternative drive assembly of the orthosis of FIG. 1.
Figure 8:
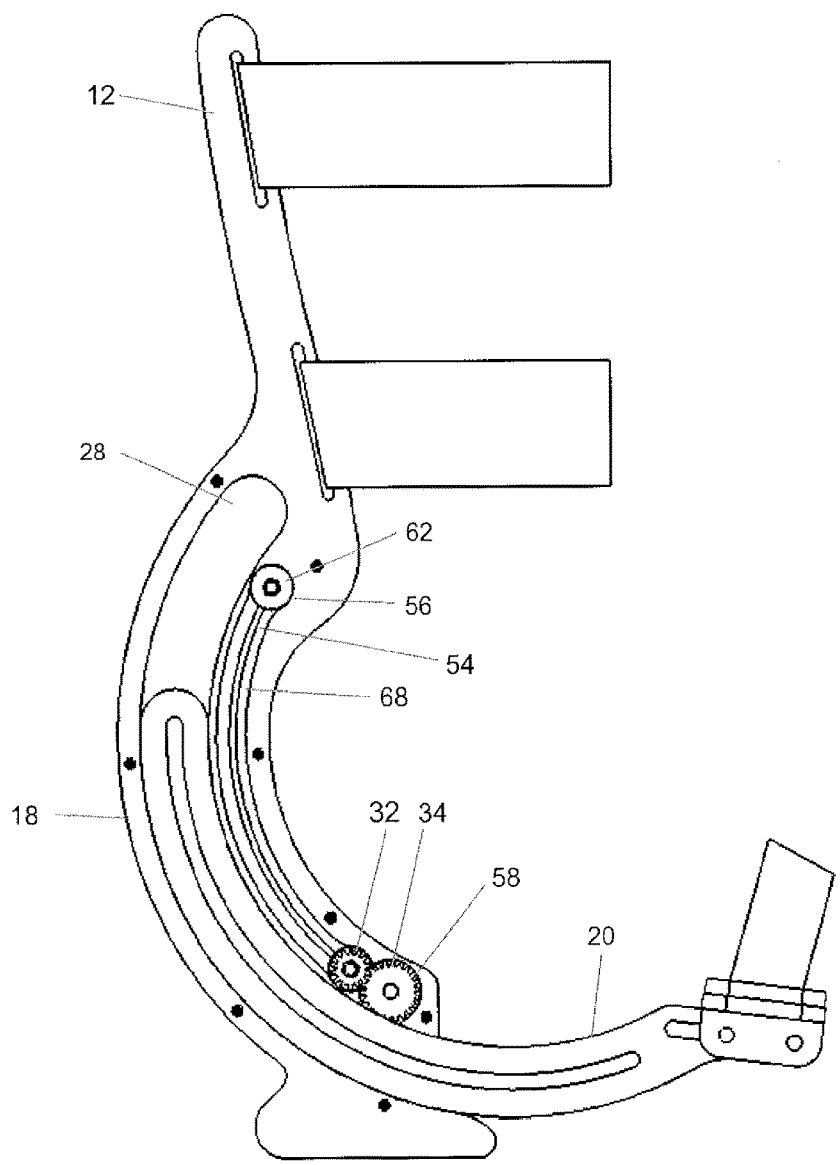
FIG. 8 depicts a side view of the drive assembly of FIG. 7.
Figure 9:
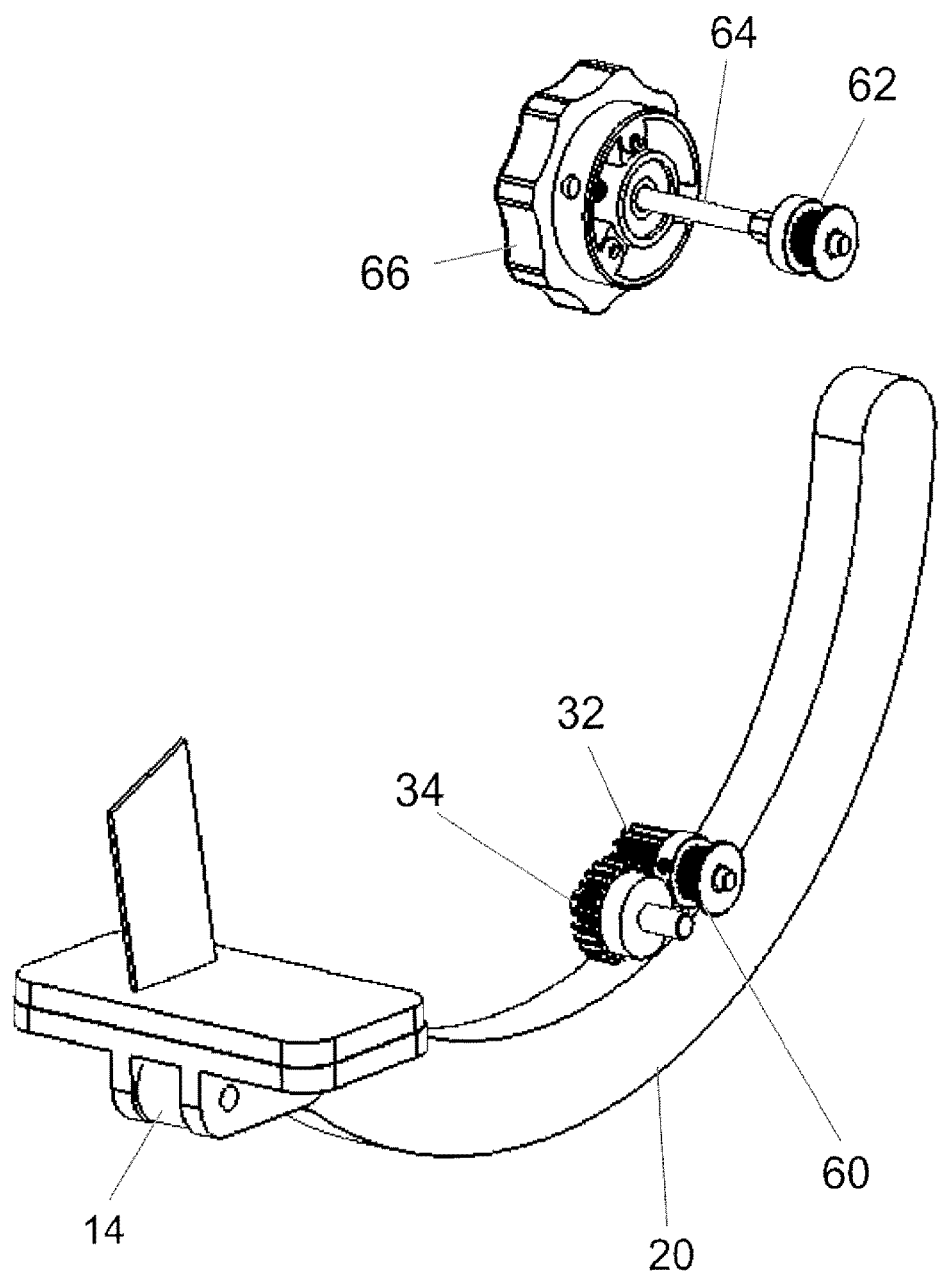
FIG. 9 depicts a rear side partial isometric view of the drive assembly of FIG. 7.

Referring to FIGS. 7 and 8, in another embodiment, the orthosis can include an alternative drive assembly 53. In the alternative drive assembly 53, the first member 12 includes a drive belt channel 54 having upper and lower end portions 56 and 58. The drive assembly 53 is positioned in the drive belt channel 54, where a drive gear 32 and a main gear 34 are positioned in the lower end portion 58 of the drive belt channel 54. Referring also to FIG. 9, a lower belt gear 60 is operable connected to the drive gear 32, such that drive gear 32 rotates with the lower belt gear 60. An upper belt gear 62 is positioned in the upper end portion 56 of the drive belt channel 54, where a drive shaft 64 is connected to the upper belt gear 62, extending through the cover plate 26. A knob 66 can be affixed to the drive shaft 64 to facilitate rotation thereof.

A drive belt 68 is positioned in the drive belt channel 54, about the upper and lower belt gears 60 and 62. A rotation of the dive shaft 64 rotates the upper belt gear 62, which in turn drives the drive belt 68 about the lower belt gear 60, rotating the drive gear 32 and the main gear 34. As previously described, the main gear 34 is sized such that a portion of the gear teeth 40 protrudes into the main channel 28 of the first extension member 18. The gear teeth 40 sufficiently protrude into the main channel 28, such that the gear teeth 40 can engage the second extension member 20. The inclusion of the drive belt 68 enables the position of the knob 66 to be moved to an upper end portion of the first extension member 18, decreasing the reaching distance for operating the orthosis 10. However, it is contemplated that the knob 66 can be optionally located to either the upper position, attached to the upper belt gear 60, or the lower position, attached to the drive gear 32, at the discretion of the user.

The drive mechanism 53 can further include a locking mechanism. The locking mechanism can be used to secure the position of the second member 14 with respect to the first member 12. The locking mechanism can prevent the actuation of the drive mechanism 53, securing the position of first and second members 12 and 14. Alternatively, the locking mechanism can secure the first and second members 12 and 14, preventing an actuation of the drive assembly 22 from moving the first and second members 12 and 14. The locking mechanism can be utilized such that the orthosis 10 can be used as a static splint.

In an alternative embodiment, the drive assembly 22 of orthosis 10 in accordance with the present disclosure can be actuated by a motor instead of by a manually actuatable member, such as the knob 38. Likewise, the motor may be configured an adapted with gearing that causes the orthosis to cycle through a range of motion in a predetermined manner, or alternatively maybe controlled by a programmable logic controller (PLC).

In an embodiment, an electric motor is mounted to the drive shaft 36 for rotation of the drive gear 32. A battery or other source of energy provides electric power to the motor. Alternatively, the motor can be supplied with external power. A microprocessor controls the operation of the motor. The microprocessor and motor together can be used to cycle the second member 14 through a plurality of positions that cause the joint to undergo a range of motion, either by dorsiflexion, by plantarflexion, or both. For example, the microprocessor may be used to move the second member 14 in one pivotal direction a certain amount, hold there while tissue stretches, then move further in that direction; or in any other manner.

In another manner of use, the orthosis 10 can be set to cycle to one end of the joint's range of motion and hold there for a predetermined period of time, then cycle to the other end of the joint's range of motion and hold there. The programming and control of the microprocessor is within the skill of the art as it relates to driving the motor to control the second member 14 to move in known manners. This embodiment is ideally suited for continuous passive motion exercise, because the orthosis 10 is portable and because the motor can be programmed with the desired sequence of movements.

It should be understood that the particular physical arrangement of the motor, the power source, and the microprocessor is not the only possible arrangement of those elements. The disclosure contemplates that other arrangements of these or similarly functional elements are quite suitable, and thus, the disclosure is intended to cover any such arrangement. Additionally, another type of power source, other than an electric motor, can also be used. For example, the use of a hydraulic or pneumatic motor as the drive assembly is contemplated.

The present disclosure can further include a monitor for use with the orthosis 10, which provides assurances the patient is properly using the orthosis 10 during his/her exercise period. For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety.

Figure 10:
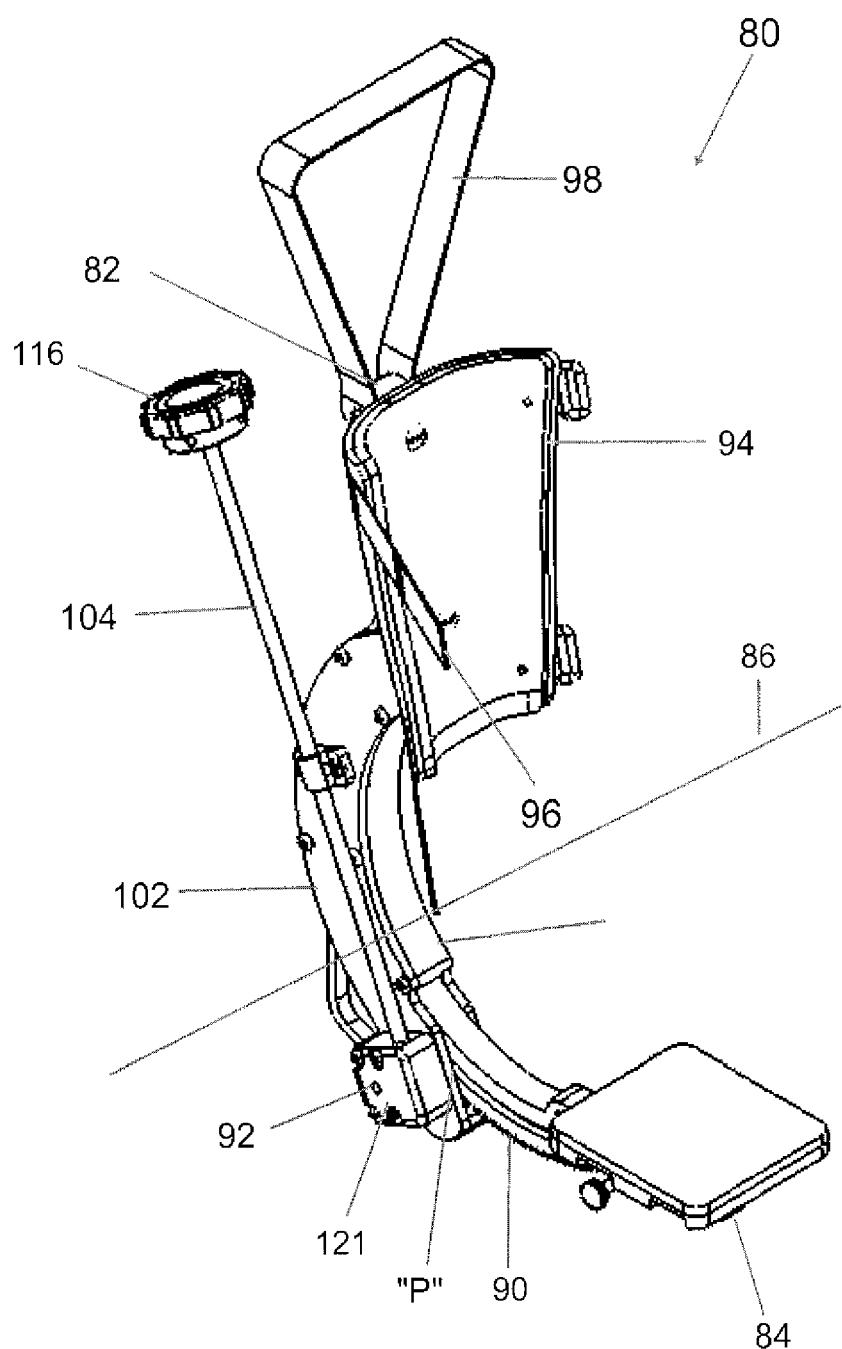
FIG. 10 depicts another orthosis of the present disclosure.

Referring to FIG. 10, another embodiment of the orthosis 80 of the present disclosure is provided. The orthosis 80 includes a first member 82 attachable to a first body portion, such as a user's lower leg. The shape and configuration of the first member 82 may be selected to support or conform generally along the lower leg of the user.

The first member 82 is operatively associated with or connected to a second member 84 so that the first and second members 82 and 84 may move or rotate with respect to each other. In use, the second member 84 may be attachable to a second body portion, such as a foot, so that the relative movement of the two members 82 and 84 also causes movement of the ankle joint. The orthosis 80 may have an axis or rotation 86 that is aligned with the axis of rotation of the joint. In this manner, the instantaneous axis of rotation (IAR) of the first and second members 82 and 84 may better match the IAR of the treated joint. The first and second members 82 and 84 are operatively connected to each other, offset from the orthosis axis 86.

The first member 82 of the orthosis 80 includes a first extension member 88 extending there from and having an arcuate shape. The second member 84 of the orthosis 80 likewise includes a second extension member 90 extending therefore and having an arcuate shape. The first and second extension members 88 and 90 are operatively connected at point "P," such that in operation the second extension member 90 travels through the first extension member 88 about an arcuate path and substantially through point "P." The arcuate shapes of the first and second extension members 88 and 90 results in the foot rotating about the orthosis axis 86, or alternatively about a moving IAR, when the second member 84 is moved from a first position to a second position relative to the first member 82, there by preventing compression of the joint.

The orthosis 80 further includes a drive assembly 92 located at or near point "P." In this embodiment, the drive assembly 92 is operably connected to the first and second extension members 88 and 90 for applying force to the first and second members 82 and 84 to pivot the second body portion about the orthosis axis 86.

In order for the orthosis 80 to flex the joint the first and second members 82 and 84 are affixed to the first and second body portions, respectively, tightly enough so that the first and second members 82 and 84 can apply torque to flex the joint. The second extension member 90 is moved through the drive assembly 92 from a first position to a second position, relative to the first extension member 88, rotating the second member 84 and the second body portion about the orthosis axis 86 stretching the joint. As the second member 84 is rotated to the second position, the second extension member 90 travels at least partially through point "P" and may travel substantially through this point for a large range of motion. Because the first and second members 82 and 84 are affixed to the first and second body portions, the outward pivoting movement of the second member 84 causes the joint to be flexed as desired. The orthosis 80 may then be maintained in the second position for a predetermined treatment time providing a constant stretch to the joint. The orthosis may alternatively be configured to impart a constant force or load on the joint or may utilize the techniques of Static Progressive Stretch as described in co-pending application Ser. No. 11/203,516, entitled "Range of Motion System and Method", and filed on Aug. 12, 2005, the entirety of which is incorporated by reference.

Returning to the example where the orthosis is maintained in the second position, after the expiration of the treatment time, the second member 84 may then be moved back to the first position, relieving the joint. Optionally, the second member 84 can be rotated to a third position, increasing the stretch on the joint, or partially reducing it to allow limited relaxation of the surrounding tissue. The second member 84 can be rotated at discrete time intervals to incrementally increase, reduce, or vary the stretch of the joint through the treatment cycle. After completion of the treatment cycle, the second member 84 is returned to the first position for removal of the orthosis 80. In operation of the orthosis 80 can be utilized to flex the joint in either dorsiflexion or plantarflexion.

The first member 82 includes a cuff 94 having a pair of straps 96 attachable about a user's lower leg. The straps 96 are sufficiently tighten to prevent relative movement between the first member 82 and the lower leg. The cuff 94 can be adjustably mounted to the first member 82 to accommodate different size legs. A knee strap 98 is provided to assist in maintaining the orthosis 80 position and orientation on the lower leg. The knee strap 98 is mounted to a top portion of the first member 82, such that when a user's leg is positioned though the strap, the strap is disposed about a lower end of the thigh of a user, proximal to the knee joint. The strap 98 can be utilized to prevent the lower leg from sliding up the device and also to be used to prevent heel lift-off.

Figure 11:
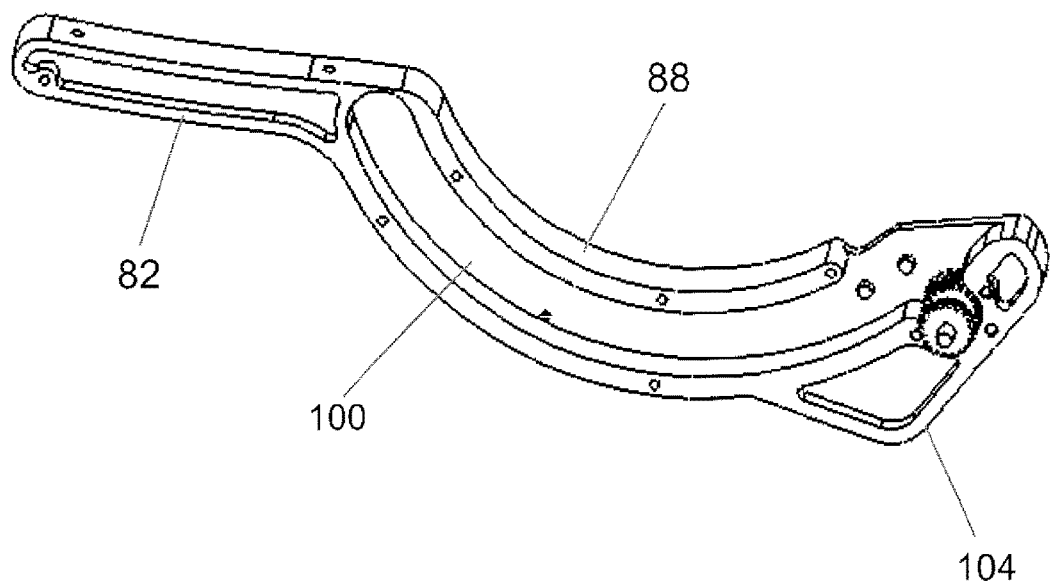
FIG. 11 depicts a sectional view of a first member of the orthosis of FIG. 10.

Referring also FIG. 11, the first extension member 88 portion of the first member 82 includes an arcuate main channel 100 extending therein. A cover plate 102 is affixable to the first extension member 88, over the main channel 100, defining a passage through which the second extension member 90 travels. The first extension member 88 can further include a base 104, where the base 104 is configured to support the orthosis 80 on a flat surface.

Figure 12:
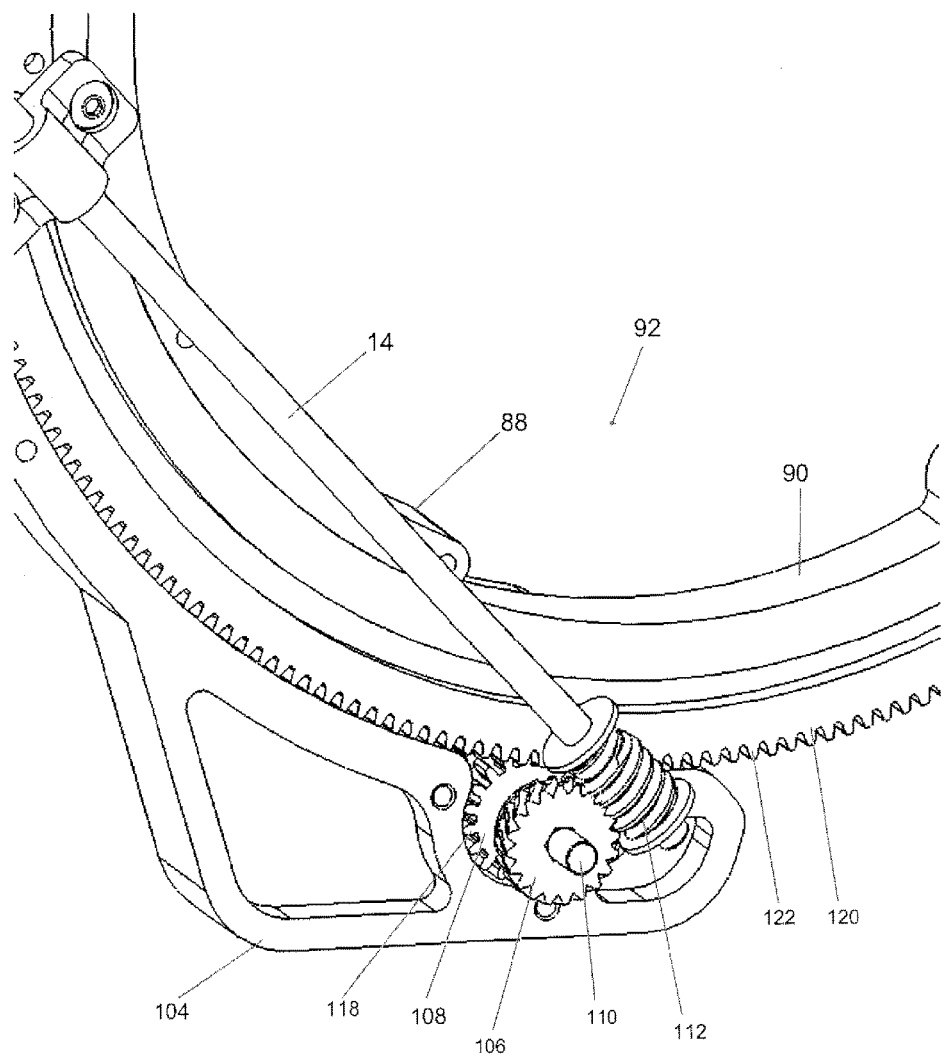
FIG. 12 depicts a sectional view of the drive assembly of the orthosis of FIG. 10.

Referring to FIG. 12, the drive assembly 92 is positioned in the first extension member 88 portion of the first member 82, proximal to the base 104. The drive assembly 92 includes drive gear 106 and a main gear 108, where the drive gear 106 and the main gear 108 are affixed to a drive axle 110. (See also FIG. 13). The main gear 108 is positioned in the first extension member 88, and covered by the cover plate 102. The drive axle 110 extends through the cover plate 102, where the drive gear 106 is affixed to the drive axle 110

A worm gear 112 is positioned in engagement with the drive gear 106, such that a rotation of the worm gear 112 rotates the drive gear 106 and subsequently the main gear 108. A drive shaft 114 is connected to the worm gear 112, extending the drive assembly 92. A knob 116 can be affixed to the drive shaft 114 to facilitate rotation thereof. A rotation of the dive shaft 114 rotates the worm gear 112, which in turn rotates the drive and main gears 106 and 108. The main gear 108 is sized such that a portion of the gear teeth 118 protrudes into the main channel 100 of the first extension member 88 portion of the first member 82. The gear teeth 118 sufficiently protrude into the main channel 100, such that the gear teeth 118 can engage the second extension member 90. A drive cover 121 can be connected to the cover plate 102, where the drive and worm gear 106 and 112 are covered by the drive cover 121. The worm gear 112 is rotatably supported in the drive cover 121 in engagement with the drive gear 106. The worm gear 112 can be utilized to prevent a backing off of the drive assembly, decreasing the stretch of the connective tissue of the joint.

The drive mechanism 92 can further include a locking mechanism. The locking mechanism can be used to secure the position of the second member 84 with respect to the first member 82. The locking mechanism can prevent the actuation of the drive mechanism 92, securing the position of first and second members 82 and 84. Alternatively, the locking mechanism can secure the first and second members 82 and 84, preventing an actuation of the drive mechanism 92 from moving the first and second members 82 and 84. The locking mechanism can be utilized such that the orthosis 80 can be used as a static splint.

Figure 13:
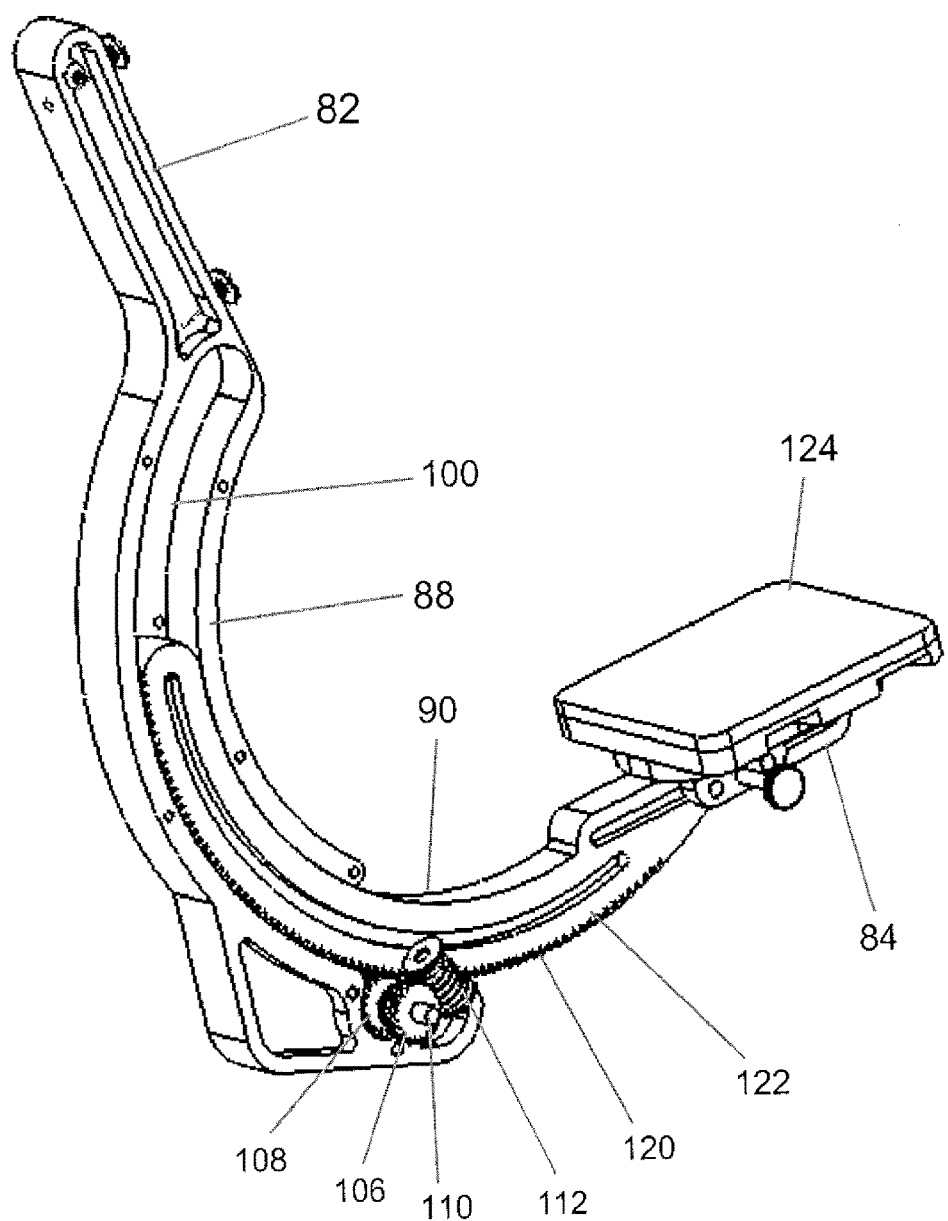
FIG. 13 depicts a partial sectional view of the orthosis of FIG. 10.

Referring to FIGS. 12 and 13, the second extension member 90 of the second member 84 includes a lower surface 120, where the upper surface 120 can include a plurality of teeth 122. The teeth 122 are sized such that the gear teeth 118 of the main gear 108 can engage the second extension member 90 and move the second extension member 90 through the passage in the first extension member 88 as the knob 116 is rotated.

Figure 14:
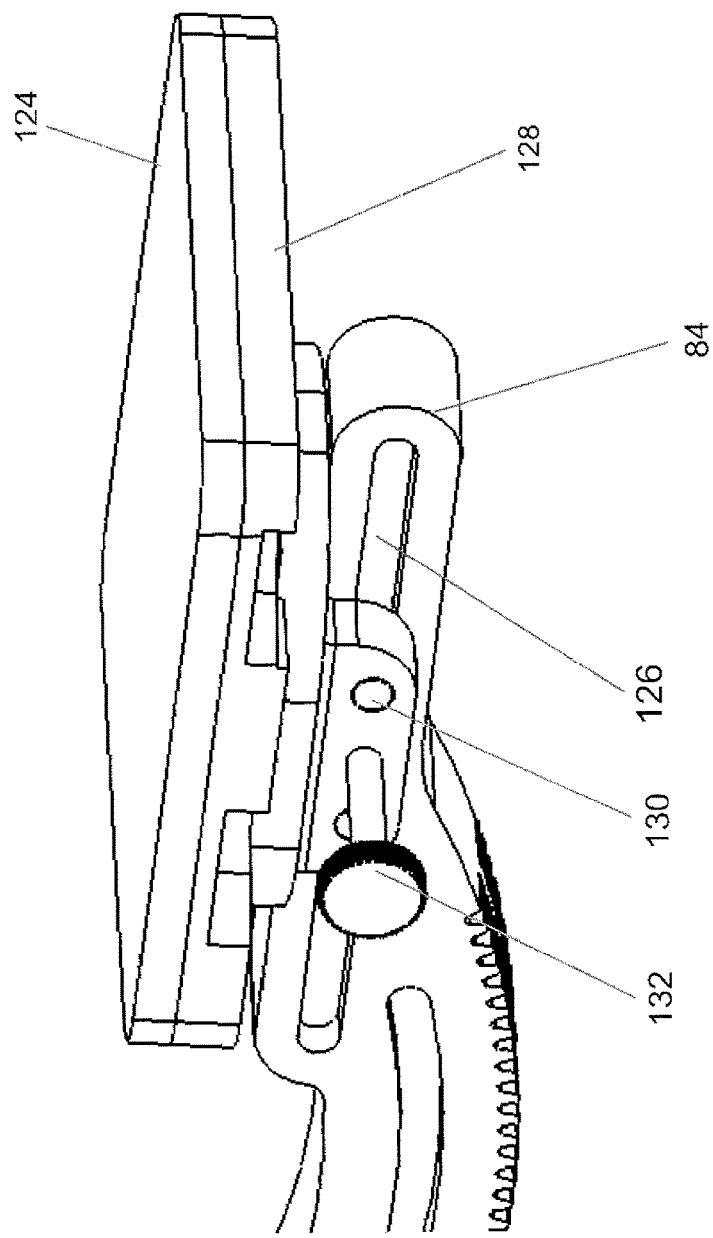
FIG. 14 depicts a foot plate of the orthosis of FIG. 10.

The second member 94 can include a foot plate 124 slidingly mounted thereon. Referring to FIG. 14, the second member 84 can include a slotted section 126. A foot plate mounting bracket 128 is slidingly positioned on the second member 84, about the slotted section 126. Pins 130 are applied to slidingly secure the mounting bracket 128 in the slotted section 126. A threaded member 132 can be threaded through the mounted bracket 128, into contact with the slotted section 146, where a tightening of the threaded member 132 can be used to secure the position of the mount bracket 126. As previously disclosed, the foot plate 124 can further include a strap attachable about a user's foot. The strap is sufficiently tightened to prevent relative movement between the foot plate 124 and the foot. The slidingly mounting of the foot plate 124 to the second member permits the foot plate to be adjustable to accommodate various size feet.

In an exemplary use, the orthosis 80 is operated to flex a joint in dorsiflexion in the following manner. The first member 82 is fastened to the lower leg and the second member 84 is fastened to the foot. The orthosis 80 is attached to the first and second body portions in a first position. The drive assembly 92 is operated to move the second member 84 from the first position to a second position, relative to the first member 82 by rotating the foot about a joint axis 86, wherein the second extension member 90 is drawn into the first extension member 88. The connective tissue of the joint is consequently stretched. The orthosis 80 is maintained in the second position for a predetermined treatment time, utilizing the principles of stress relaxation to stretch the connective tissue of the joint. Additionally, the second extension member 90 can be made of a substantially rigid but flexible material, such that while in the second position the second extension member 90 acts like a spring, providing dynamic stretch to the connective tissue of the joint. After the expiration of the treatment time, the second member 84 may be returned to the first position, relieving the joint.

Optionally, the second member 84 can be rotated to a third position, further increasing the stretch of the connective tissue of the joint. The second member 84 can be rotated at discrete time intervals to incrementally increase the stretch of the joint through the treatment cycle. After completion of the treatment cycle, the second member 84 is returned to the first position relieving the joint.

In an exemplary use, the orthosis 80 is operated to flex a joint in plantarflexion the following manner. The first member 82 is fastened to the lower leg and the second member 84 is fastened to the foot. The orthosis 80 is attached to the first and second body portions in a first position. The drive assembly 92 is operated to move the second member 84 from the first position to a second position, relative to the first member 82 by rotating the second body portion about a joint axis 86, wherein the second extension member 90 is extended from the first extension member 88. The connective tissue of the joint is consequently stretched. The orthosis 80 is maintained in the second position for a predetermined treatment time, utilizing the principles of stress relaxation to stretch the connective tissue of the joint. Additionally, the second extension member 90 can be made of a substantially rigid but flexible material, such that while in the second position the second extension member 90 acts like a spring, providing dynamic stretch to the connective tissue of the joint. After the expiration of the treatment time, the second member 84 may be returned to the first position, relieving the joint.

Optionally, the second member 84 can be rotated to a third position, further increasing the stretch of the connective tissue of the joint. The second member 84 can be rotated at discrete time intervals to incrementally increase the stretch of the joint through the treatment cycle. After completion of the treatment cycle, the second member 84 is returned to the first position relieving the joint.

Figure 15:
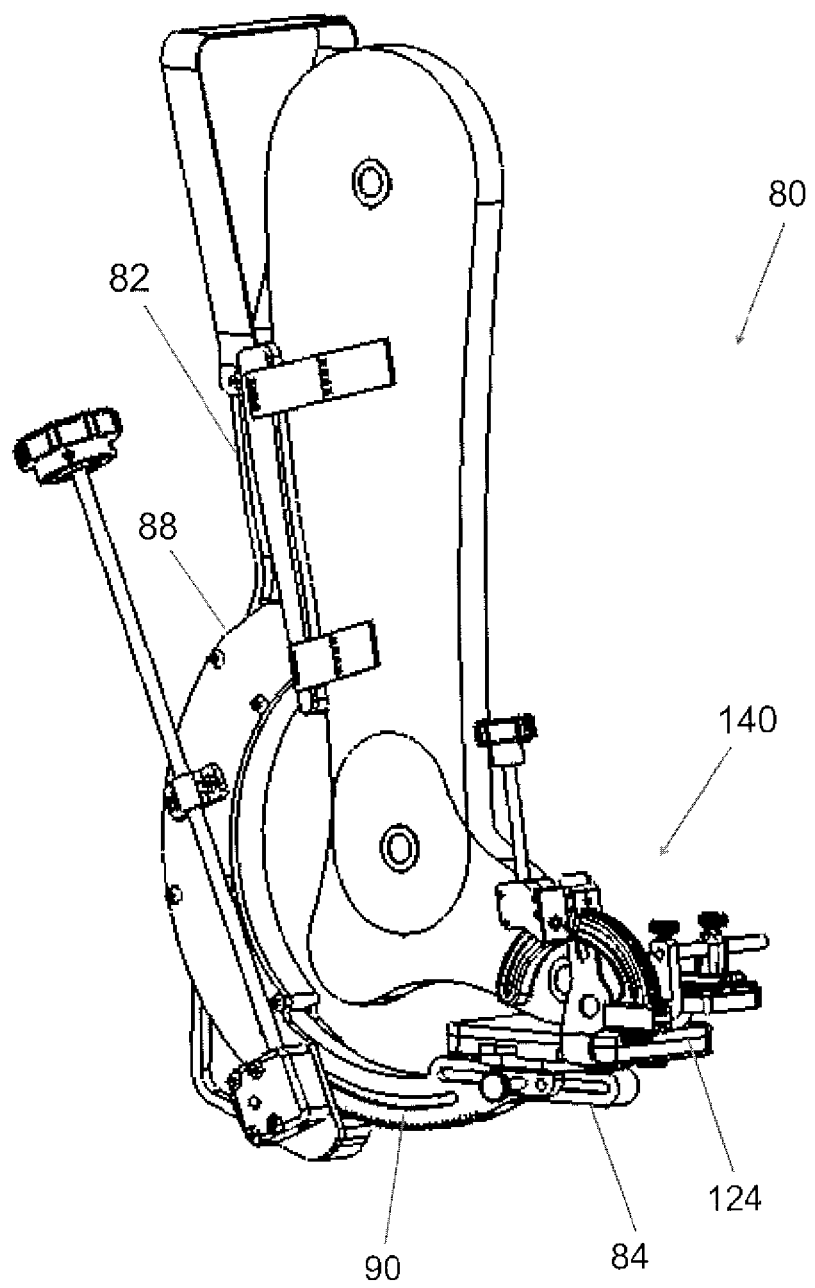
FIG. 15 depicts the orthosis of FIG. 10 including a toe assembly.

Referring to FIG. 15, the orthosis 80 can further include a toe assembly 140 attached to the foot plate 124. It is understood by those skilled in the art that the other joints of the toe assembly 140 may be flexed or extended the toe, without departing from the spirit and scope of the disclosure. Additionally, the toe assembly 140 is described in use on the "big" toe or hallux on the foot. However, it should be understood by those skilled in the art that the toe assembly 140 is equally applicable for use on the second, third, fourth and minimus toes of the foot.

Each toe in the foot extends from the metatarsal bone and is formed by the proximal phalanx, middle phalanx, and distal phalanx, each of which is respectively pivotally connected to form a joint there between. The toe assembly 140 may be configured to flex or extend (or both) a toe joint, where the joint defines an inner sector on the flexor side that decreases in angle as the joint is flexed (bent) and an outer sector on the extensor side that decreases in angle as the joint is extended (straightened). The toe assembly 140 may be configured as described in co-pending application Ser. No. 11/261,424, entitled "Range of Motion," filed on Oct. 28, 2005, and PCT International Application No. PCT/US06/60228, entitled "Range of Motion Device," filed on Oct. 27, 2008 the entirety of which are incorporated by reference.

Figure 16:
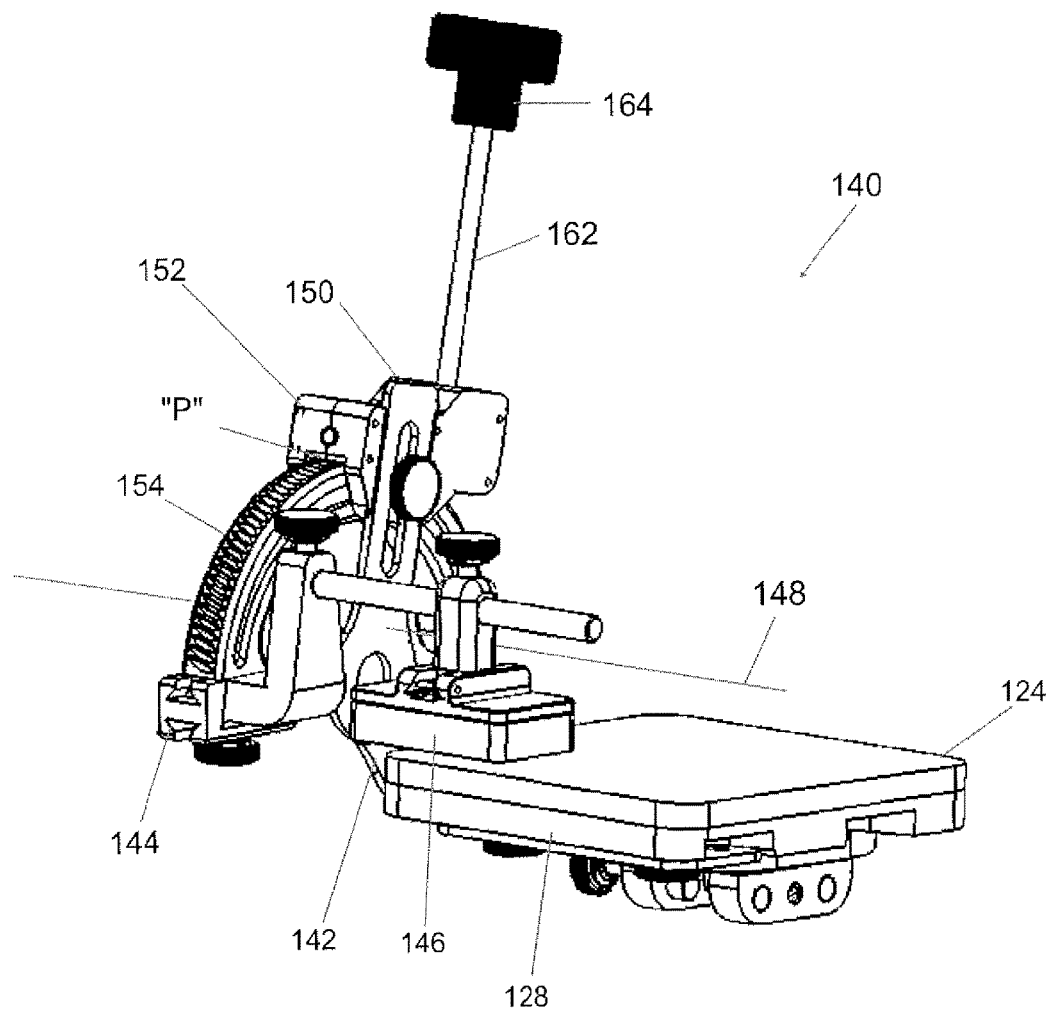
FIG. 16 depicts a front isometric view of the toe assembly.
Figure 17:
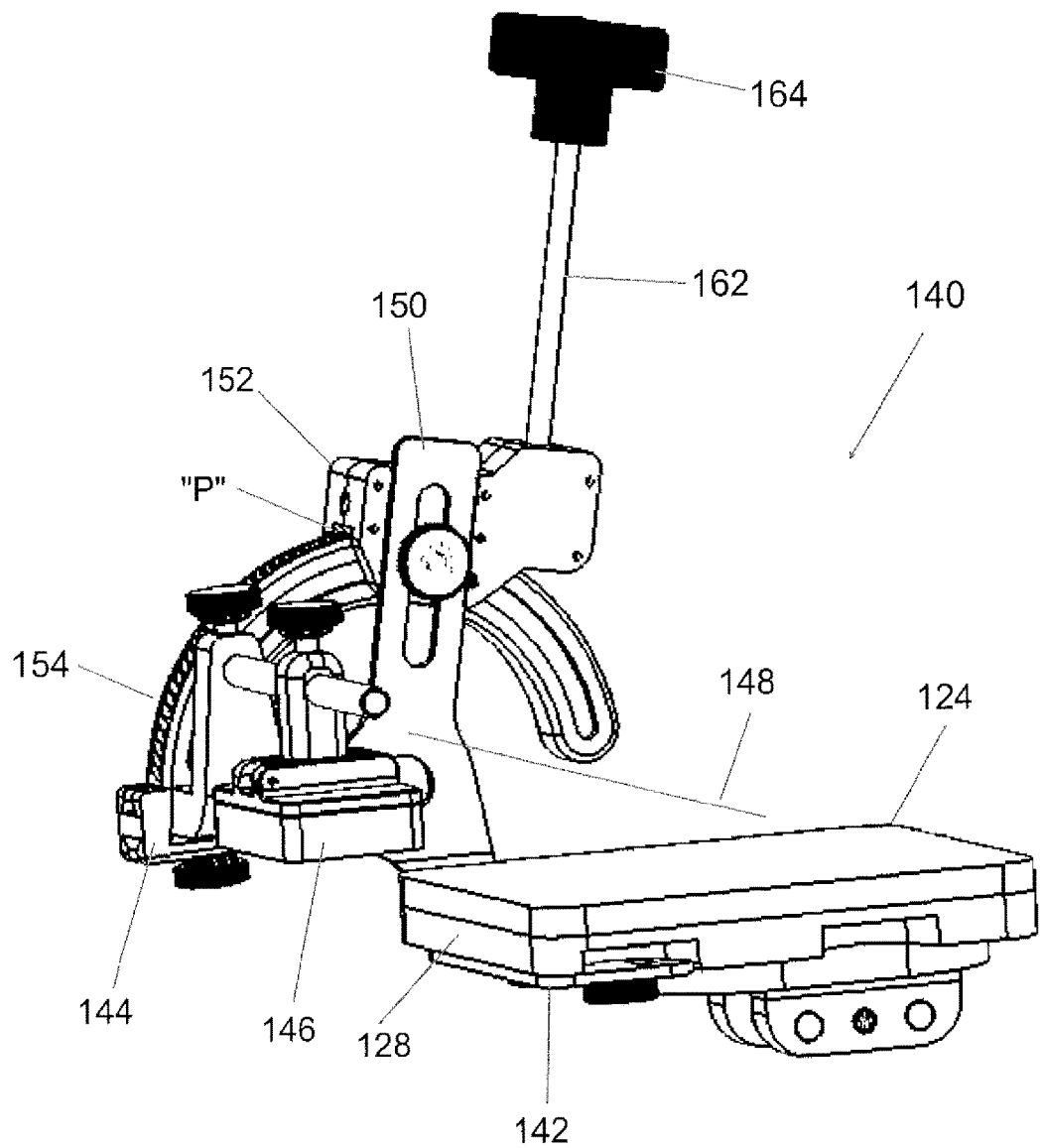
FIG. 17 depicts a side isometric view of the toe assembly.

Referring to FIGS. 16-17, a toe assembly 140 of the present disclosure includes a first member 142 affixable to the foot plate mounting bracket 128 and a second member 144 having a toe cuff 146 attachable to a toe of the user's foot, wherein the second member 144 is rotatable with respect to the first member 142 about an axis of rotation 148. The toe cult 146 can be sized to attach to a single toe or multiple toes. The first and second members 142 and 144 are attached to the foot and toe of the user, such that as the second member 144 is rotated about the axis of rotation 148, the toe is rotated about a joint axis.

A first extension member 150 is affixed to and extends from the first member 142, wherein a drive assembly 152 is positioned on an end portion of the first extension member 150. A second extension member 154 is similarly affixed to and extends from the second member 144, wherein the second extension member 154 has an arcuate shape. The second extension member 154 engages the drive assembly 152 of the first extension member 150 at a point "P." An actuation of the drive assembly 152 operates to move the second extension member 154 through the drive assembly 152, such that the toe cuff 146 travels along an arcuate path with respect to the first member 142. The arcuate shape of the second extension member 154 results in the toe rotating about the joint axis, as the toe cuff 146 is moved along the arcuate path "A." the drive assembly 152 can be actuated to move the toe cuff 146 and toe from a first position to a second position relative to the foot plate 124. Once again, the term "cuff" as used herein means any suitable structure for transmitting the force of the toe assembly 140 to the limb portion it engages.

The first extension member 150 can extend substantially vertically from the first member 142 or extend at an angle .alpha. from the first member 142, where the angle .alpha. and the radius of curvature of the second extension member 154 (if constant) can be configured such that the axis of rotation 148 is aligned with the joint axis of rotation. The curvature of the second extension member 154 need not be constant, and therefore the axis of rotation may shift or move in a manner that preferably mimics or approximates the moving IAR the joint would normally have. Another potential benefit of the toe assembly 140 having the capability of a moving IAR is when multiple joints are being treated by the device. For instance, the range of motion of the tip of a toe may involve cooperative motion of two or more joints. If the combined bending of the multiple joints causes the overall motion to rotate about a moving axis, it would be beneficial for the toe assembly 140 to approximate this moving IAR. Thus, the curvature of the second extension member 154 may be complex in order to better approximate a moving IAR.

Figure 18:
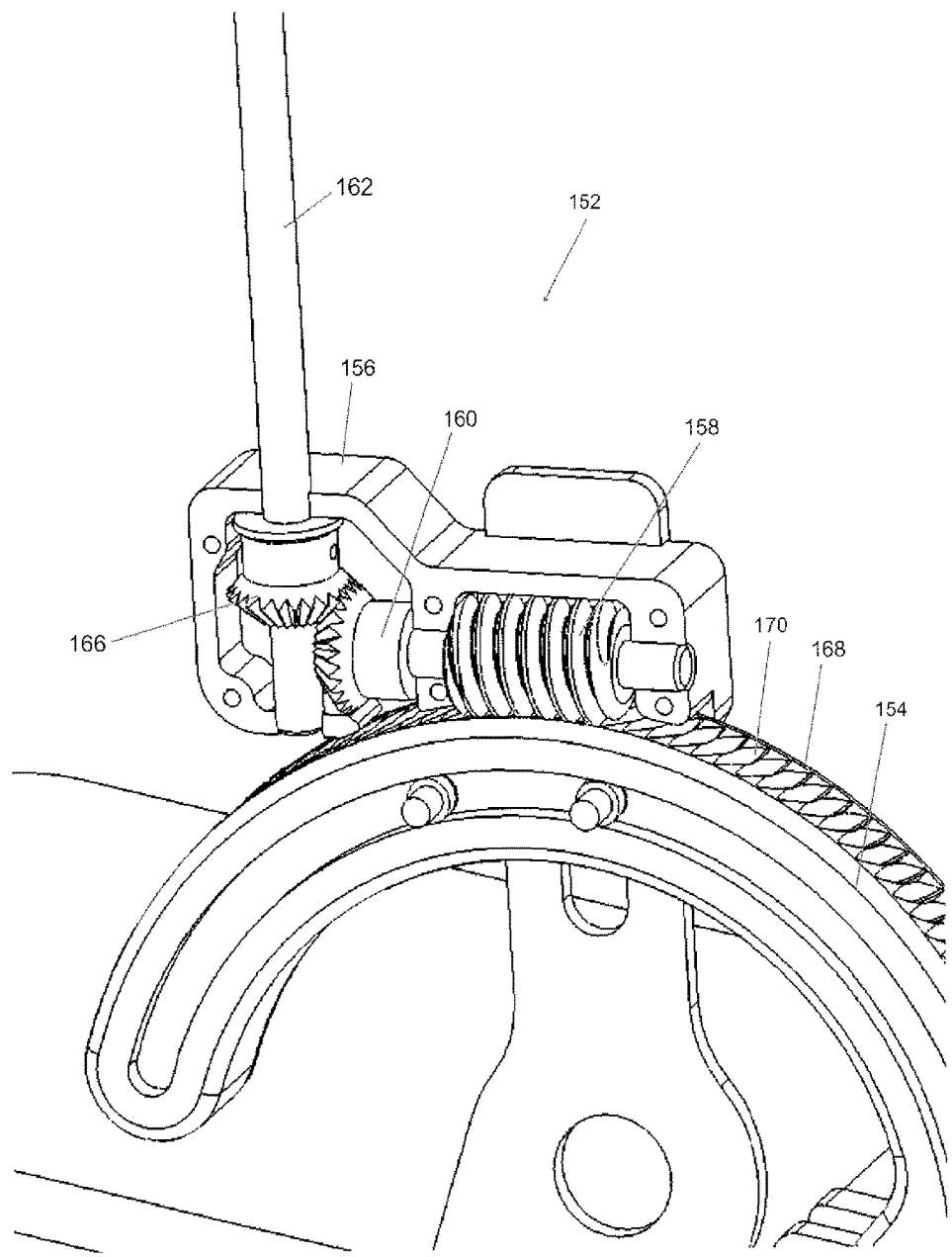
FIG. 18 depicts the drive assembly of the toe assembly.

Referring to FIG. 18, the drive assembly 152 can include a housing 156 having a worm gear 158 therein. A first miter gear 160 is attached to the worm gear 158 such that a rotation of the first miter gear 160 rotates the worm gear 158. The drive assembly 152 further includes a drive shaft 162 have a knob 164 at one end and a second miter gear 166 at an opposite end. The second miter gear 166 is positioned within the housing 156, in engagement with the first miter gear 160. A rotation of the knob 165 rotates the drive shaft 162 and the second miter gear 166, which in turn rotates the first miter gear 160 and the worm gear 158.

A gear surface 168 of the second extension member 154 includes a plurality of teeth 170. The second extension member 154 is positioned throughout the housing 156, such that the worm gear 158 engages the teeth 170 of the second extension member 154. A rotation of the knob 164 rotates the worm gear 148, which in turn moves the second extension member 154 through the housing 156.

In an exemplary use, toe assembly 140 is operated to rotate a toe about a joint axis in the following manner. The foot plate 124 is fastened to the foot with one or more straps, laces, or similar retaining device. Similarly, the toe cuff 146 is fastened securely to the toe of the user, such that the joint and joint axis 148 is interposed between the foot plate 124 and the toe cuff 146. The toe assembly 140 is attached to the toot and toe in a first position. The drive assembly 152 is actuated to move the second extension member 154, such that the toe cuff 146 travels along an arcuate path from the first position to a second position, relative to the foot plate 124, rotating the toe about the joint axis stretching the joint. The toe assembly 140 is maintained in the second position for a predetermined treatment time providing a constant stretch to the joint. Additionally, the second extension member 154 can be made of a substantially rigid but material, such that while in the second position the second extension member 154 acts like a spring, providing dynamic stretch to the connective tissue of the joint.

After the expiration of the treatment time, the toe cuff 146 is moved back to the first position, relieving the joint. Optionally, the toe cuff 146 can be rotated to a third position, thereby increasing or decreasing the stretch on the joint. The toe cuff 146 can be rotated at discrete time intervals to incrementally increase the stretch of the joint through the treatment cycle. After completion of the treatment cycle, the toe cuff 146 is returned to the first position for removal of the toe assembly 140.

Figure 19:
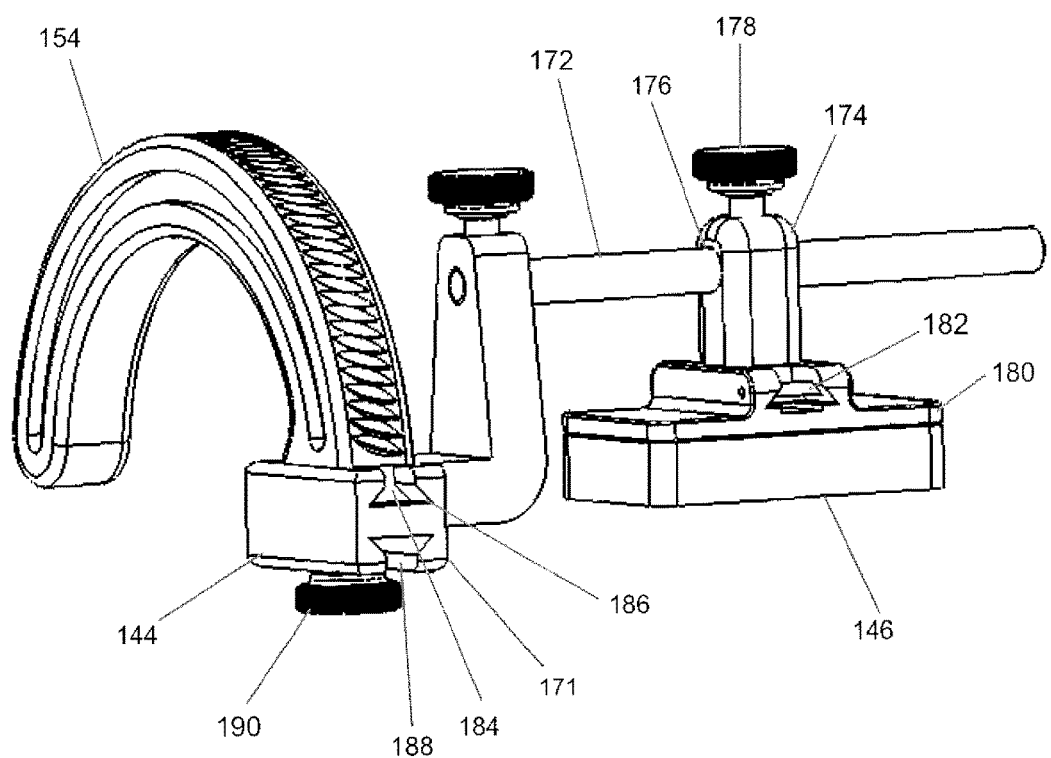
FIG. 19 depicts the toe cuff of the toe assembly.

Referring to FIG. 19, the second extension member 154 can include an attachment bracket 171 for adjustably attaching the toe cuff 146 to the second extension member 154. The attachment bracket 171 can include a toe rod 172 extending there from. The toe cuff 146 can be slideably mounted on the toe rod 172 to position toe cuff 146 over the toe. Alternatively, the toe rod 172 can be of sufficient length such that the toe cuff 146 can be slidingly positioned on a selected toe on the foot of the user, for example, the big toe, minimus toe, or any toe there between.

The toe cuff 146 can be positioned on the toe rod 172 with a first bracket 174, where the toe rod 172 passes through a passage 176 in the first bracket 174. A set screw 178 is provided to secure the first bracket 174 to the toe rod 172. When the set screw 178 is loosened, the first bracket 174 is free to slide along the toe rod 172. A tightening of the set screw 178 secures the first bracket 174 in place on the toe rod 172.

The toe cuff 146 can further include a second bracket 180, where the second bracket 180 can be pivotally mounted to the first bracket 174. For example, the second bracket 180 can be attached to the first bracket 174 with a pin or screw connector, allowing the second bracket 180 to rotate with respect to the first bracket 174.

Additionally, when a joint is flexed or extended a compressive force may be applied to the connective tissue surrounding the joint. It may be desirable to control the compressive force, distracting the joint as the joint is flexed or extended. "Distraction" is defined by one dictionary as "separation of the surfaces of a joint by extension without injury or dislocation of the parts." (Taber's Cyclopedic Medical Dictionary, 16th Edition, 1989, page 521), and involves stretching rather than compressing the joint capsule, soft tissue, ligaments, and tendons.

Additionally, the second bracket 180 can be slideably mounted to the first bracket 174. For example the second bracket 180 can be mounted to the first bracket 174 with a dovetail joint 182, allowing the second bracket 180 to slide with respect to the first bracket 174. The sliding movement of the toe cuff 146 helps to limit the distractive or compressive forces which can be imparted on the joint by the rotation of the toe cuff 146 with respect to the foot plate 124.

The attachment bracket 171 can be mounted to the second extension member 154 with a dovetail joint 184, where the attachment bracket 171 includes upper and lower joint section 186 and 188. The upper and lower joint sections 186 and 188 allow the attachment bracket 171 to be attached to the second extension member 154 in either a flexed or extension position. Additionally, the dove tail joint 184 allows the attachment bracket 171 to slide with respect to the second extension member 154. The sliding movement of the attachment bracket 171 helps to limit the distractive or compressive forces which can be imparted on the joint by the rotation of the toe cuff 146 with respect to the foot plate 124. A set screw 190 is positionable through the attachment bracket 171, engaging the second extension member 154, such that the set screw 190 can be used to control the position of the attachment bracket 171 with respect to the second extension member 154.

The adjustable connection of the toe cuff 146 to the attachment bracket 171 and the adjustable connection of the attachment bracket 171 to the second extension member 154 can be used to align the toe cuff 146 with the toe. The alignment of the toe cuff 146 on the toe can be used to substantially limit the force applied to the toe to that of a torque about the joint axis 148.

In operation of the toe assembly 140 to extend the joint, the toe assembly 140 starts at a more flexed position. The attachment bracket 171 is attached to the second extension member 154 such that the toe cuff 146 engaged the toe of the user for movement in extension. The foot plate 124 and toe cuff 146 are attached onto the foot and toe portions, respectively. The second extension member 154 is moved through the drive assembly 150 from the first position to a second position, relative to the first extension member 142, rotating the toe cuff 146 and the toe about the axis 148 stretching the joint. As the toe cuff 146 is rotated to the second position the second extension member 154 travels along an arcuate path about and substantially through point "P." The toe assembly 140 is maintained in the second position for a predetermined treatment time providing a constant stretch to the joint.

As the toe assembly 140 is rotated from the first position to the second position, extending the joint, the toe cuff 146 moves along the first bracket 174. Because the foot plate 124 and toe cuff 146 are clamped onto the foot and toe as described above, the outward pivoting movement of the toe cuff 146 causes the joint to be extended as desired. However, this extension of the joint can place strong distractive forces on the soft tissues around the joint. The sliding movement of the toe cuff 146 helps to limit these distractive forces by counteracting the outward movement. Thus, the detrimental effects of strong distractive forces normally generated in forced extension of a joint are avoided, being replaced with the beneficial effects of limited and controlled distraction.

In operation of the toe assembly 140 to flex the joint, the toe assembly 140 starts at a more extended position. The attachment bracket 171 is attached to the second extension member 154 such that the toe cuff 146 engages the toe of the user for movement in flexion. The foot plate 124 and toe cuff 146 are attached onto the foot and toe portions, respectively. The second extension member 154 is moved through the drive assembly 150 from the first position to a second position, relative to the first extension member 142, rotating the toe cuff 146 and the toe about the axis 148 stretching the joint. As the toe cuff 146 is rotated to the second position the second extension member 154 travels along an arcuate path about and substantially through point "P." The toe assembly 140 is maintained in the second position for a predetermined treatment time providing a constant stretch to the joint.

As the toe assembly 140 is rotated from the first position to the second position, extending the joint, the toe cuff 146 moves along the first bracket 174. Because the foot plate 124 and toe cuff 146 are clamped onto the foot and toe as described above, the inward pivoting movement of the toe cuff 146 causes the joint to be flexed as desired. However, this flexion of the joint can place strong compressive forces on the soft tissues around the joint. The sliding movement of the toe cuff 146 helps to limit these compressive forces by counteracting the inward movement. Thus, the detrimental effects of strong compressive forces normally generated in forced flexion of a joint are avoided, being replaced with the beneficial effects of limited and controlled compression.

Figure 20:
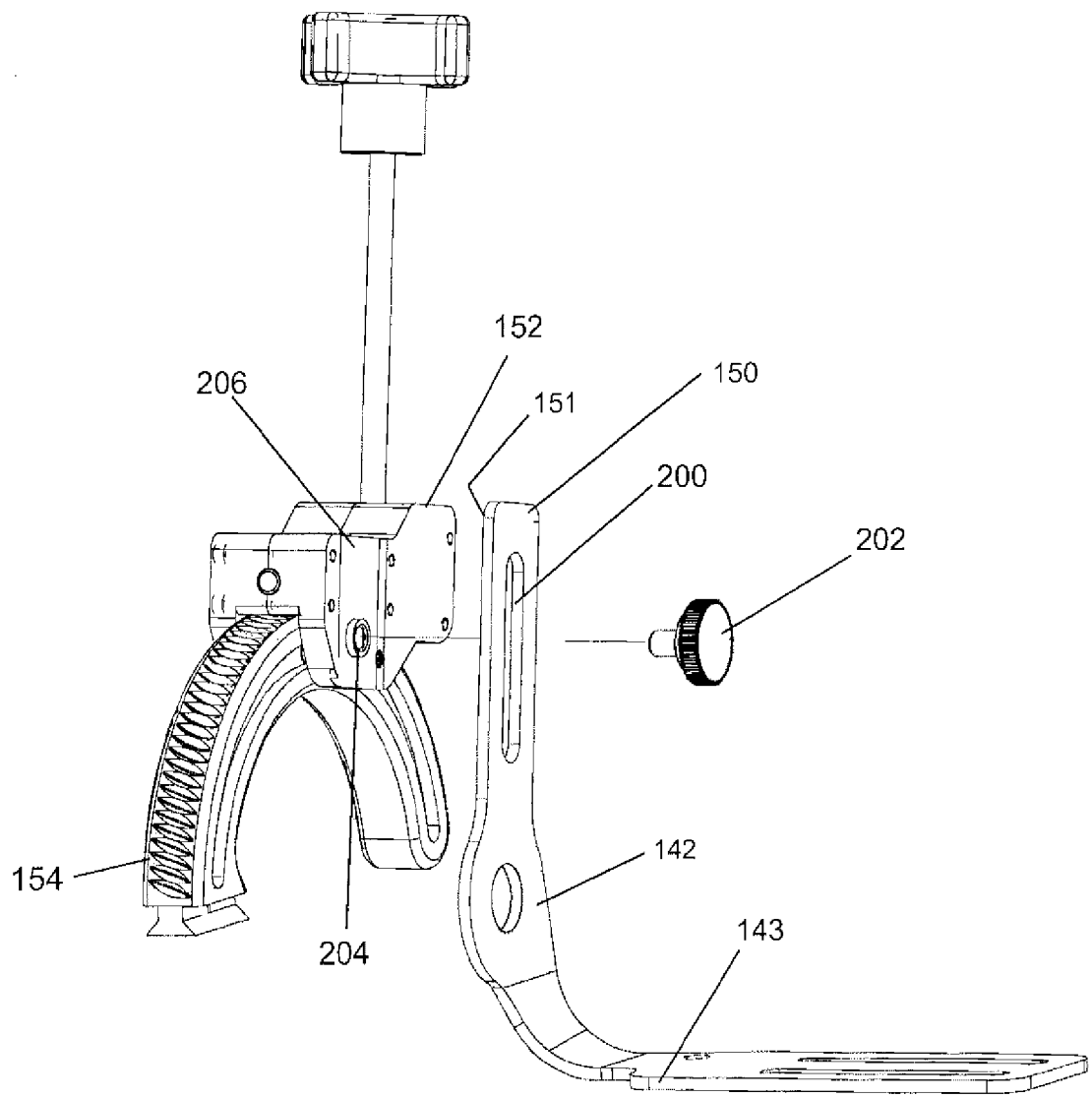
FIG. 20 is an exploded view of the drive assembly connection to the first member of the toe assembly.

Referring to FIG. 20, the drive assembly 152 can be adjustable mounted to the first extension member 150. The first extension member 150 includes a longitudinal slotted section 200. A threaded member 202 is positioned through the longitudinal slotted section 200, where the threaded member 202 is threaded into a threaded hole 204 in the drive assembly 152. The position of the drive assembly 152 is secured on the first extension member 150 by tightening the threaded member 202, compressing the first extension member 150 between the threaded member 202 and the drive assembly 152. The position of the drive assembly 152 can be adjusted by loosening the threaded member 202 and sliding the drive assembly 152 along the longitudinal slot 200. In this manner the position of the drive assembly 152 can be adjusted to align the axis of rotation 148 with the joint axis.

The drive assembly 220 can further includes an indented portion 206. The indented portion 206 in sized to receive the first extension member 150 therein, such that the first extension member 150 slides through the indented portion 206 as the drive assembly 152 is moved along the first extension member 152. The indented portion 206 is configured to align the drive assembly 152 with respect to the first extension member 150. The indented portion 206 provides the further benefit of resisting a rotation of the drive assembly 152 with respect to the first extension member 150 when the toe assembly 140 is in use.

Figure 21:
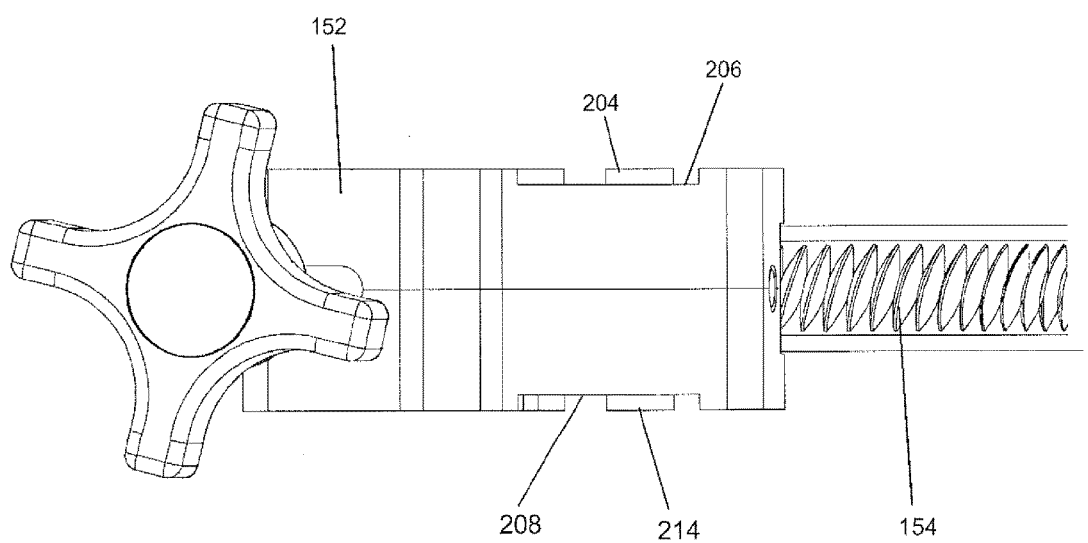
FIG. 21 is a top view of the drive assembly of the toe assembly.

Referring to FIG. 21, the drive assembly 152 can include a pair of indented portions 206 and 208, positioned on opposite sides on the drive assembly 152. As shown in FIG. 20, the first indented section 206 can be used to position the drive assembly 152 in an outer position on the toe assembly 140, where the drive assembly 152 is positioned on an outside surface 151 of the first extension member 150.

Figure 22:
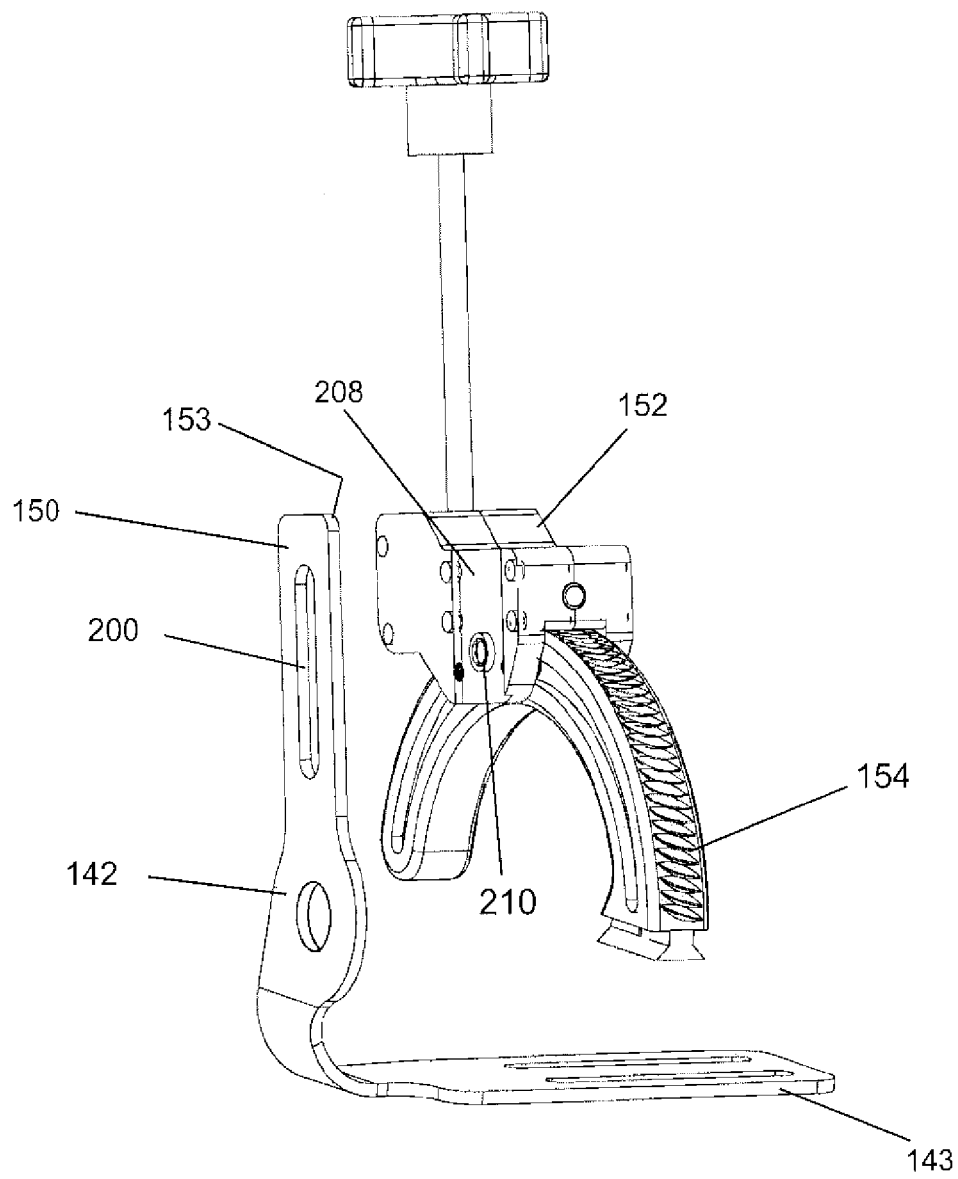
FIG. 22 is an exploded view of another drive assembly connection to the first member of the toe assembly.

Alternatively, as shown in FIG. 22, the second indented section 208 can be used to position the drive assembly 152 in an inner position on the toe assembly 140, where the drive assembly 152 is positioned on an inner surface 153 of the first extension member 150. The threaded member 202 is positioned through the longitudinal slotted section 200, where the threaded member 202 is threaded into a second threaded hole 214 in the drive assembly 152.

In an embodiment, the first member 142 can be adjustable mounted to the foot plate 124, such that the position of the toe cuff 146 can be adjusted to align the toe cuff 146 with a toe of interest and the joint axis of the toe. In instances were the joint of a toe is misaligned, for example for toe deformations such as hammer toe, bunion, etc, the linear and angular position of the toe cuff 146 can be adjusted with respect to the foot plate 124 aligning the toe cuff 146 with the misaligned toe such that the axis of rotation 148 of the toe assembly 140 is aligned with the axis of rotation of the toe joint. In the manner, the toe assembly 140 can be adjusted to prevent the unwanted application of torsional forces to the toe joint.

Figure 23:
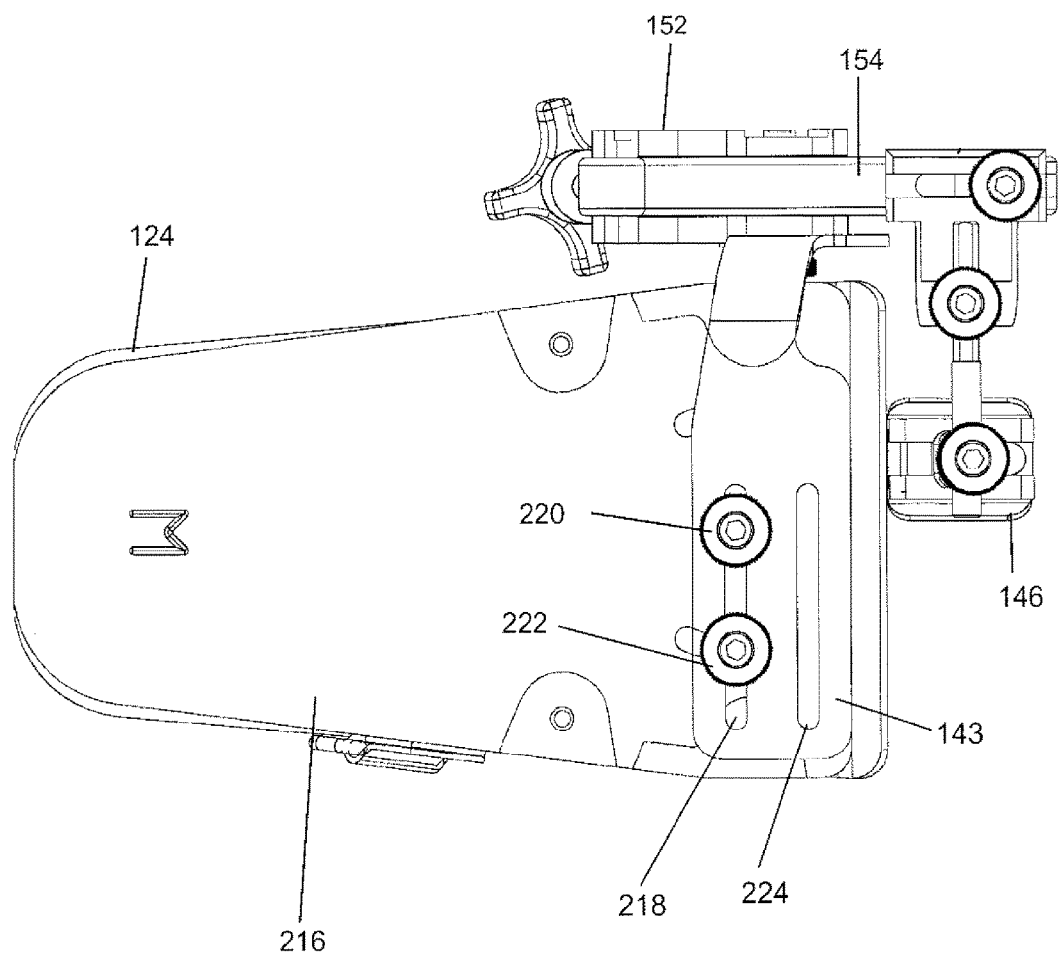
FIG. 23 depicts a bottom view of the toe assembly.

Referring to FIG. 23, the first member 142 is adjustably attached to a bottom surface of the foot plate 124. The first member 142 includes a second, substantially horizontal, extension member 143 having a longitudinal slot 218, through which a pair of threaded members 220 and 222 are positioned, attaching the first member 142 to the foot plate 124, second extension member 143 can be moved along the longitudinal slot 218 to laterally adjust the position of the first member 142 with respect to the foot plate 124. The first member 142 is secured in position by tightening the threaded member 220 and 222, compressing the second extension member 143 between the threaded members 220 and 222 and the bottom surface 216 of the foot plate 124.

The second extension member 143 can further include a second longitudinal slot 224, parallel and offset from the first longitudinal slot 218. The second extension member 143 can be attached to the foot plate 124, using the second longitudinal slot 224 to longitudinally adjust the position of the first member 142 with respect to the foot plate 124. Similarly, the second extension member 143 can be moved along the second longitudinal slot 224 to laterally adjust the position of the first member 142 with respect to the foot plate 124.

Figure 24:
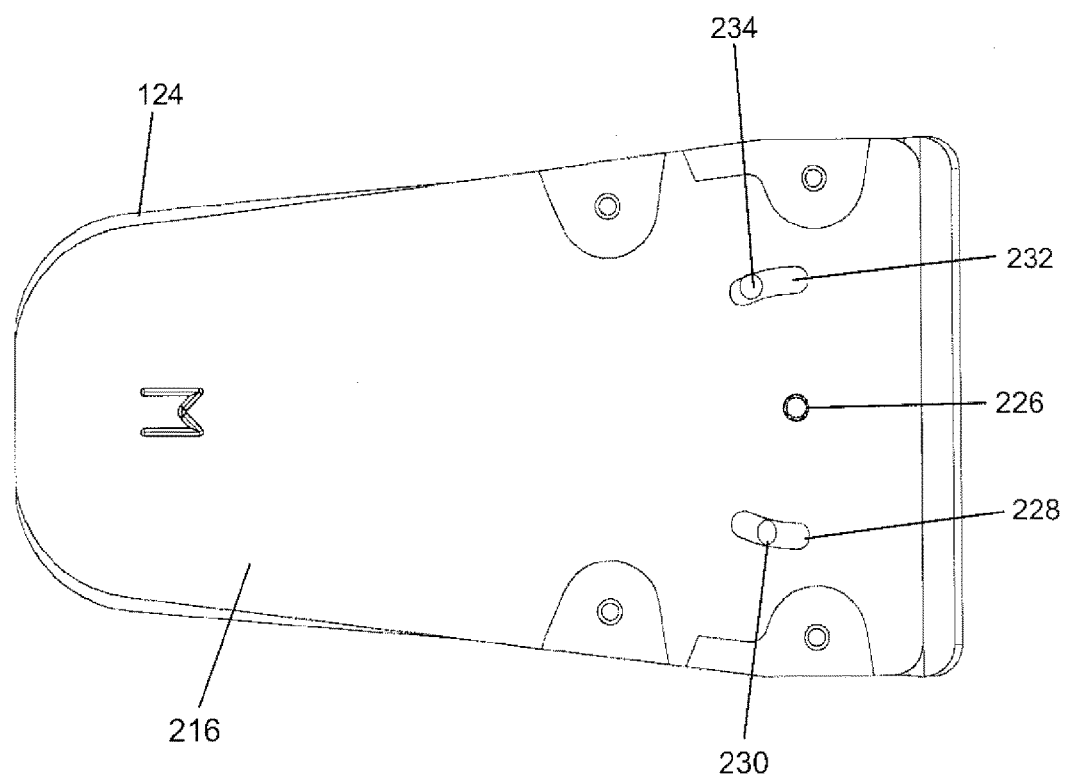
FIG. 24 depicts a bottom view of a first cuff of the toe assembly.

It is also contemplated that the angular position of the first member 142 can be adjusted with respect to the foot plate 124. In an embodiment, as shown in FIG. 24, the bottom surface 216 of the foot plate 124 includes a center threaded hole 226 and an arcuate slot 228. An internally threaded fastener 230 is slidingly positioned in the arcuate slot 228, opposite the bottom surface 216. The first member 142 is attached to the foot plate 124 by positioning the threaded members 220 and 222 through a longitudinal slot 218 or 224 of the second extension member 143 and engaging the threaded hole 226 and the internally threaded fastener 230 in the arcuate slot 228. The angular position of the first member 142 can be adjusted with respect to the foot plate 124 by pivoting the second extension member 143 about threaded member 220 in the center threaded hole 226, such that the internally threaded fastener 230 and the second threaded member 220 travel along the arcuate slot 228. The first member 142 is secured in position by tightening the threaded members 220 and 222, compressing the second extension member 143 between the threaded members 220 and the bottom surface 216 of the foot plate 124, and compressing the second extension member 143 and foot plate 124 between threaded member 222 and internally threaded fastener 230.

The bottom surface 216 of the foot plate 124 can further include a second arcuate slot 232, where an internally threaded fastener 234 is slidingly positioned in the second arcuate slot 232, opposite the bottom surface 216 of the foot plate 124. Similar to arcuate slot 228, second arcuate slot 232 can be used to angularly adjust the position of the first member 143 with respect to the foot plate 124.

Specifically, the first member 142 is attached to the foot plate 124 by positioning the threaded members 220 and 222 through a longitudinal slot 218 or 224 of the second extension member 143 and engaging the threaded hole 226 and the internally threaded fastener 234 in arcuate slot 232. The angular position of the first member 142 can be adjusted with respect to the foot plate 124 by pivoting the second extension member 143 about threaded member 220 in the center threaded hole 226, such that the internally threaded fastener 234 and the second threaded member 222 travel along the arcuate slot 232. The first member 142 is secured in position by tightening the threaded member 220 and 222, compressing the second extension member 143 between the threaded members 220 and the bottom surface 216 of the foot plate 124, and compressing the second extension member 143 and foot plate 124 between the threaded member 222 and internally threaded fastener 234.

It is also contemplated that the first member 142 can be attached to the foot plate 124 using the arcuate slots 228 and 232 and the respected internally threaded members 230 and 234. Specifically, the first member 142 is attached to the foot plate 124 by positioning the threaded members 220 and 222 through a longitudinal slot 218 or 224 of the second extension member 143 and engaging the internally threaded fastener 230 in the arcuate slot 228 and the internally threaded fastener 234 in arcuate slot 232. The angular position of the first member 142 can be adjusted with respect to the foot plate 124 by pivoting the second extension member 143 such that the internally threaded fasteners 230 and 234 travel along the arcuate slots 228 and 232. The first member 142 is secured in position by tightening the threaded member 220 and 222, the second extension member 143 and foot plate 124 between the treaded members 220 and 222 and internally threaded fastener 230 and 234.

While the embodiment discussed above utilize a second extension member having an arcuate shape to control movement of the second member, it should be understood that skilled artisans having the benefit of this disclosure will appreciate that other configurations may likewise provide similar relative movement.

The components of the present disclosure are rigid members made of, for example, aluminum, stainless steel, polymeric, or composite materials. The member and extensions are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

All references cited herein are expressly incorporated by reference in their entirety.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. An orthosis for stretching tissue about an ankle joint of a patient comprising:
    a first member configured to be secured to a lower leg of the patient;
    a second member movably connected to the first member and configured to be secured to a foot of the patient, the second member including a gear; and
    a drive assembly coupled to the gear of the second member, the drive assembly configured to drive movement of the gear to move the second member with respect to the first member, wherein movement of the second member relative to the first member at least one of flexes and extends the ankle joint when the first member is secured to the lower leg of the patient and the second member is secured to the foot of the patient.

2. The orthosis set forth in claim 1, wherein the first member includes a first arm and a lower leg cuff secured to the first arm.

3. The orthosis set forth in claim 2, wherein the second member includes a second arm and a foot plate secured to the second arm.

4. The orthosis set forth in claim 3, wherein the second arm is movable connected to the first arm.

5. The orthosis set forth in claim 1, wherein drive assembly includes a drive gear rotatably mounted on the first member and operably coupled to the gear of the second member.

6. The orthosis set forth in claim 5, wherein the drive gear is manually rotatable for selectively moving the second member with respect to the first member.

7. The orthosis set forth in claim 6, wherein the drive gear includes a worm.

8. The orthosis set forth in claim 7, wherein the drive assembly includes a knob for manually rotating the drive gear.

9. The orthosis set forth in claim 8, wherein the worm engages the gear of the second member.

10. The orthosis set forth in claim 9, wherein the drive assembly include a drive shaft secured to the knob.

11. The orthosis set forth in claim 1, wherein the drive assembly includes a locking assembly.

12. The orthosis set forth in claim 1, further comprising a toe orthosis attached to the second member.

13. The orthosis set forth in claim 12, wherein the toe orthosis includes a toe cuff sized and shaped to engage a toe of the user.

14. The orthosis set forth in claim 13, wherein the toe orthosis includes a toe drive assembly configured to drive movement of the toe cuff relative to the second member such that the toe cuff imparts movement of the toe of the user during use of the toe orthosis.

* * * * *